United States Patent
Hennies et al.

(10) Patent No.: US 7,105,538 B2
(45) Date of Patent: Sep. 12, 2006

(54) 2-PYRROLIDIN-2-YL-[1,3,4]-OXADIAZOLE COMPOUNDS AND THEIR USE AS ANTI-DEPRESSANTS

(75) Inventors: Hagen-Heinrich Hennies, Simmerath (DE); Corinna Sundermann, Aachen (DE); Helmut Buschmann, Esplugues de Llobregat (ES); Bernd Sundermann, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 11/066,981

(22) Filed: Feb. 28, 2005

(65) Prior Publication Data

US 2005/0187260 A1    Aug. 25, 2005

Related U.S. Application Data

(63) Continuation of application No. PCT/EP03/09390, filed on Aug. 25, 2003.

(30) Foreign Application Priority Data

Aug. 20, 2002   (DE) ................. 102 40 818

(51) Int. Cl.
```
A61K 31/4725    (2006.01)
A61K 31/44      (2006.01)
A61K 31/4245    (2006.01)
C07D 217/18     (2006.01)
C07D 413/04     (2006.01)
C07D 271/10     (2006.01)
```
(52) U.S. Cl. ............... 514/314; 514/340; 514/364; 546/135; 546/269.4; 548/143
(58) Field of Classification Search ............. 548/131, 548/143; 546/256, 135, 269.4; 514/364, 514/333, 314, 340
See application file for complete search history.

(56) References Cited

U.S. PATENT DOCUMENTS

| | | | |
|---|---|---|---|
| 3,912,747 A | 10/1975 | Huguet et al. | |
| 4,784,998 A | 11/1988 | Yevich | |
| 6,809,107 B1 * | 10/2004 | Kanojia et al. | 514/312 |

FOREIGN PATENT DOCUMENTS

| JP | 2001-247569 | 9/2001 |
|---|---|---|
| WO | WO 01/04116 | 1/2001 |
| WO | WO 01/04116 A2 | 1/2001 |
| WO | WO 02/02554 | 1/2002 |
| WO | WO 02/02554 A1 | 1/2002 |

OTHER PUBLICATIONS

A. C. Jung et al., The Efficacy of Selective Serotonin Reuptake Inhibitors for the Management of Chronic Pain, Journal of General Internal Medicine, 1997, pp. 384-389, vol. 12, No. 6, ISSN: 0884-9734.
R. Berard et al., The Appropriate Use of Antidepressants in the Cancer Setting: A Review, International Medical Journal, 1996, pp. 257-259, vol. 3, No. 4, ISSN: 1341-2051.
Patrick Onghena et al., "Antidepressant-Induced Analgesia in Chronic Non-Malignant Pain: a Meta-Analysis of 39 Placebo-Controlled Studies", Pain, 1992, pp. 205-219, vol. 49, Elsevier Science Publishers B.V.
H.J. McQuay et al., "A Systematic Review of Antidepressants in Neuropathic Pain", Pain Medicine Journal Club Journal, 1997, pp. 119-122, vol. 3, No. 3, Lippincott-Raven Publishers, Philadelphia, PA, USA.
Susanna Borg et al., Synthesis of 1,2,4-Oxadiazole-, 1,3,4-Oxadiazole-, and 1,2,4- Triazole-Derived Dipeptidomimetics, J. Org. Chem., 1995, pp. 3112-3120, vol. 60, 1995 American Chemical Society.
Christopher T. Brain et al., "Synthesis of 1,3,4- Oxadiazoles Using Polymer-Supported Reagents", Synlett, 2001, pp. 382-284, No. 3, Thieme Stuttgart, New York, USA, ISSN 0936-5214.
German Search Report Aug. 11, 2005 based on German patent application No. 102 40 818.1, filed Aug. 30, 2002.

* cited by examiner

*Primary Examiner*—Kamal A. Saeed
*Assistant Examiner*—Michael P. Barker
(74) *Attorney, Agent, or Firm*—Crowell & Moring LLP

(57) ABSTRACT

Substituted 2-pyrrolidin-2-yl compounds corresponding to formula I

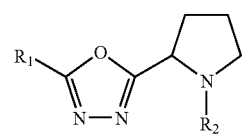

a method for their production, pharmaceutical compositions containing them, and methods of using them, especially for treating pain and/or depression.

9 Claims, No Drawings

2-PYRROLIDIN-2-YL-[1,3,4]-OXADIAZOLE COMPOUNDS AND THEIR USE AS ANTI-DEPRESSANTS

CROSS REFERENCE TO RELATED APPLICATIONS

This application is a continuation of international patent application No. PCT/EP2003/009390, filed Aug. 25, 2003, designating the United States of America, and published in German as WO 2004/024725 on Mar. 25, 2004, the entire disclosure of which is incorporated herein by reference. Priority is claimed based on Federal Republic of Germany patent application no. DE 102 40 818.1, filed Aug. 30, 2002.

BACKGROUND OF THE INVENTION

The present invention relates to substituted 2-pyrrolidin-2-yl-[1,3,4]-oxadiazole compounds, to methods for their production, to pharmaceutical compositions containing these compounds and to the use of these substances for producing pharmaceutical compositions, preferably for the treatment of depression, and to methods of treating depression.

Depression is an affectivity disorder, in which a depressive syndrome predominates, depression being associated with a depressive mood or indicating a sad disposition. The anti-depressants used for treatment are also important adjuvants for pain therapy (van Schayck et al., MMP 1998, Vol. 21, issue 10, 304–313; Jung et al., J. Gen. Intern. Med. 1997, 12/6, 384–389; Onghena and Van Houdenhove, Pain 1992, 49, 205–219; Feuerstein, Der Schmerz 1997, 11, 213–226; Rowbotham, The Pain Medicine Journal Club 1997, 3/3, 119–122), in particular for chronic pain conditions, as the prolonged burden of pain may lead to a depressive mood in the patient. This is particularly frequently the case in patients suffering from pain with cancer (Berard, Int. Med. J. 1996, 3/4, 257–259). As there have previously been no painkillers with a clinically relevant anti-depressive active component, the anti-depressants have to be added as a medication supplementary to the analgesic dose. As patients with chronic pain frequently require a large number of different medicines, the additional dose of the anti-depressant is a further burden to the organism. For this reason and to increase compliance, an analgesically effective substance with an anti-depressive active component would be particularly advantageous.

The basis of the anti-depressive efficacy is the inhibition of serotonin re-uptake.

Various substituted 2-pyrrolidin-2-yl-[1,3,4]-oxadiazole derivatives are known from the literature. Common to all of them is the fact that they are used for the treatment of neuronal diseases.

The synthesis of substituted 2-pyrrolidin-2-yl-[1,3,4]-oxadiazole derivatives has already been described by Borg et al. (J. Org. Chem. 1995, 60, 3112–3120), natural amino acids being used as the starting material and dehydration of diacylhydrazines taking place, and by Brain et al. (Synlett 2001, No. 3, 382–384), the cyclodehydration of 1,2-diacyl-hydrazines being carried out under microwaves using a polystyrene-supported dehydration agent. These syntheses are solid phase syntheses.

WO 01/04116 describes another way of synthesising pyrrolidine or piperidine derivatives for the treatment and prevention of neuronal diseases.

JP 2001247569 also describes the production of pyrrolidine or piperidine derivatives and their use for the prophylaxis and/or treatment of diseases, which are accompanied by damage to the nerves or neurodegeneration.

SUMMARY OF THE INVENTION

The object of the invention was to make available a new structural class of analgesically effective substances which are also suitable, in particular, for the treatment of depression and/or anxiolysis.

It has surprisingly been found that substituted 2-pyrrolidin-2-yl-[1,3,4]-oxadiazole derivatives of general formula I have a pronounced anti-depressive and analgesic effect.

The invention therefore relates to substituted 2-pyrrolidin-2-yl-[1,3,4]-oxadiazole derivatives corresponding to formula I,

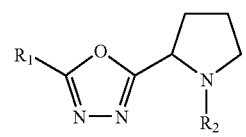

wherein
$R_1$ represents aryl or heteroaryl,
$R_2$ represents H, $SO_2R^3$ or $COR^4$; wherein
$R^3$ and $R^4$ independently of one another represent $C_{1-10}$ alkyl, $C_{3-10}$ cycloalkyl, $(C_{1-6}$ alkyl)-$C_{3-10}$ cycloalkyl, aryl, $(C_{1-6}$ alkyl)-aryl, heterocyclyl, radicals of carboxylic acid esters with 3–10 carbon atoms, dimethylamide or $NR^5R^6$, wherein
$R^5$ and $R^6$ independently of one another represent H or aryl.
Preferably in compounds according to formula I
$R_1$ represents aryl or heteroaryl, wherein
  aryl represents unsubstituted phenyl or phenyl substituted by F, Cl, O-alkyl or phenyl and
  heteroaryl represents pyridinyl or thienyl,
$R_2$ represents H, $SO_2R^3$ or $COR^4$, wherein
  $R^3$ and $R^4$ independently of one another represent $C_{1-10}$ alkyl, $C_{3-10}$ cycloalkyl, $(C_{1-6}$ alkyl)-$C_{3-10}$ cycloalkyl, aryl, $C_{1-6}$ alkyl)-aryl, heterocyclyl, radicals of carboxylic acid esters with 3–10 carbon atoms, dimethylamide or $NR^5R^6$, wherein
$C_{1-10}$ alkyl represents methyl, propyl, butyl, butenyl, isobutyl, pentyl, pent-3-yl, hept-3-yl, hept-4-yl, 2,2-dimethyl-propyl, $CH_2OCH_3$, $CH_2O(CH_2)_2OCH_3$, or $CH$(benzyl) $NSO_2C_6H_4CH_3$,
$C_{3-10}$ cycloalkyl represents cyclopropyl, cyclobutyl, cyclopentyl, adamantan-1-yl, 2-phenyl-cyclopropyl or 4,7,7-trimethyl-2-oxa-bicyclo[2.2.1]heptan-3-on-1-yl,
$(C_{1-6}$ alkyl)-$C_{3-10}$ cycloalkyl represents $CH_2$-cyclopentyl, $(CH_2)_2$-cyclopentyl or 7,7-dimethyl-1-methyl-bicyclo[2.2.1]heptan-2-one, aryl represents phenyl, benzyl or naphthyl, unsubstituted, singly substituted or multiply identically or differently substituted by phenyl, $NO_2$, $C_{1-6}$ alkyl, of which the carbon atom chain is optionally interrupted by one or more of the heteroatoms N, O or S, preferably by O, O-alkyl, $CO_2$-alkyl, $C(=O)C_{1-6}$ alkyl, $CH_2OC(=O)C_6H_5$, F, Cl, Br, $N(CH_3)_2$, $OCF_3$, $CF_3$, $SCHF_2$, $SCF_3$ or $(C=O)CH_3$,
$(C_{1-6}$ alkyl)-aryl represents 3,4-dimethoxyphenyl-$CH_2$, 4-chlorophenyl-$CH_2$, phenyl-CH=CH, benzyl-$OCH_2$, phenyl-$(CH_2)_2$, 2-bromophenyl-$CH_2$, 1-phenyl-propyl, 2-chlorophenyl-CH=CH, 3-trifluoromethyl-phenyl-CH=CH, phenoxy-CH$_2$, phenoxy-(CH$_2$)$_3$ or phenoxy-CH(CH$_3$), heterocyclyl represents pyridinyl, isoxazole, thienyl, furanyl, triazole, benzo-oxadiazole, thiadiazole, pyrazole or isoquinoline unsubstituted, singly substituted or multiply identically or differently substituted by Cl, C$_{1-6}$ alkyl, phenyl, which is in turn unsubstituted or singly substituted or multiply identically or differently substituted by Cl or C$_{1-6}$ alkyl, CF$_3$, C(=O)CF$_3$ or SCH$_3$, the radicals of carboxylic acid esters with 3–10 carbon atoms represent CH$_3$OC(=O)CH$_2$
CH$_3$OC(=O)(CH$_2$)$_3$
CH$_3$CH$_2$OC(=O)CH$_2$
CH$_3$CH$_2$OC(=O)(CH$_2$)$_2$
CH$_3$C(=O)OCH$_2$
CH$_3$C(=O)OC(CH$_3$)$_2$ or
CH$_3$C(=O)OCH(C$_6$H$_5$)

and

R$^5$ and R$^6$ independently of one another represent H or aryl, wherein aryl represents benzyl or phenyl, respectively singly or multiply identically or differently substituted by F, Cl, O-alkyl, CN, CF$_3$ or OCF$_3$.

Particularly preferred are compounds of formula I, in which

R$_1$ represents phenyl, bisphenyl-4-yl, 3-methoxyphenyl, 4-chlorophenyl, 2-fluorophenyl, pyridin-3-yl, pyridin-4-yl or thiophen-2-yl, R$_2$ represents H, SO$_2$R$^3$ or COR$^4$, wherein R$^3$ and R$^4$ independently of one another represent CH$_3$CH$_2$OCO(CH$_2$)$_2$, 2,4-dimethoxy-phenyl, 2-chloro-pyridin-3-yl, 2-chloro-pyridin-4-yl, 7,7-dimethyl-1-methyl-bicyclo[2.2.1]heptan-2-one, 3-dimethyl-amino-phenyl, 3,4-dimethoxy-phenyl, 2,5-dimethoxy-phenyl, 4-chloro-phenyl, —CH(benzyl)NSO$_2$C$_6$H$_4$CH$_3$, 4,5-dichloro-thiophen-2-yl, 2,4,6-trimethylphenyl, 4-chloro-phenoxy-methyl; C$_6$H$_5$CH=CH—, 5-methyl-2-phenyl-2H-[1,2,3] triazol-4-yl, 2,4-difluorophenyl, 2,6-difluorophenyl, 4-bromo-phenyl, 4-ethoxy-phenyl, 4-trifluoromethoxy-phenyl, 2,5-bis-trifluoromethyl-phenyl, 1-phenyl-5-propyl-1H-pyrazol-4-yl, 3-methoxy-phenyl, 2-methyl-6-trifluoromethyl-pyridin-3-yl, 4-trifluoromethylsulfanyl-phenyl, 2,2,2-trifluoro-1-3,4-dihydro-1H-isoquinoline-2-yl-ethanone or NR$^5$R$^6$, wherein R$^5$ and R$^6$ independently of one another represent H or 3-methoxyphenyl, 4-methoxyphenyl, 4-ethoxyphenyl, 2,5-dimethoxy-phenyl, 2,5-dichlorophenyl, 2,5-difluorophenyl, 4-fluorobenzyl, 4-chloro-3-trifluoromethyl-phenyl, 4-trifluoromethoxy-phenyl or 3-cyanophenyl.

The following substituted 2-pyrrolidin-2-yl-[1,3,4]-oxadiazole compounds are particularly preferred:

4-oxo-4-[2-(5-pyridin-4-yl-[1,3,4]oxadiazol-2-yl)-pyrrolidin-1-yl]-butyric acid ethyl ester
(2,4-dimethoxy-phenyl)-[2-(5-pyridin-4-yl-[1,3,4]oxadiazol-2-yl) -pyrrolidin-1-yl]-methanone
(2-chloro-pyridin-3-yl)-[2-(5-pyridin-4-yl-[1,3,4]oxadiazol-2-yl)-pyrrolidin-1-yl-]-methanone
7,7-dimethyl-1-[2-(5-pyridin-4-yl-[1,3,4]oxadiazol-2-yl)-pyrrolidin-1-sulfonylmethyl]-bicyclo[2.2.1]heptan-2-one
(3-dimethylamino-phenyl)-[2-(5-pyridin-3-yl-[1,3,4]oxadiazol-2-yl)-pyrrolidin-1-yl]-methanone
2-(3,4-dimethoxy-phenyl)-1-[2-(5-pyridin-4-yl-[1,3,4]oxadiazol-2-yl)-pyrrolidin-1-yl]-ethanone
[2-(5-biphenyl-4-yl-[1,3,4]oxadiazol-2-yl)-pyrrolidin-1-yl]-(4-chloro-phenyl)-methanone
N-{1-benzyl-2-oxo-2-[2-(5-pyridin-4-yl-[1,3,4]oxadiazol-2-yl) -pyrrolidin-1-yl]-ethyl}-4-methyl-benzylsulfonamide
4-{5-[1-(4,5-dichloro-thiophene-2-sulfonyl)-pyrrolidin-2-yl]-[1,3,4]oxadiazol-2-yl}-pyridine
3-{5-[1-(2,5-dimethoxy-benzylsulfonyl)-pyrrolidin-2-yl]-[1,3,4]oxadiazol-2-yl}-pyridine
2-(2-fluoro-phenyl)-5-[1-(2,4,6-trimethyl-benzylsulfonyl)-pyrrolidin-2-yl]-[1,3,4]oxadiazole
2-(4-chloro-phenoxy)-1-[2-(5-pyridin-4-yl-[1,3,4]oxadiazol-2-yl) -pyrrolidin-1-yl]-ethanone
3-phenyl-1-[2-(5-phenyl-[1,3,4]oxadiazol-2-yl)-pyrrolidin-1-yl]-propenone
(5-methyl-2-phenyl-2H-[1,2,3]triazol-4-yl)-[2-(5-pyridin-4-yl-[1,3,4]oxadiazol-2-yl)-pyrrolidin-1-yl]-methanone
3-{5-[1-(2,4-difluoro-benzylsulfonyl)-pyrrolidin-2-yl]-[1,3,4]oxadiazol-2-yl}-pyridine
(4-bromo-phenyl)-[2-[5-(3-methoxy-phenyl)-[1,3,4]oxadiazol-2-yl]-pyrrolidin-1-yl}-methanone
(2-chloro-pyridin-4-yl)-{2-[5-(3-methoxy-phenyl)-[1,3,4]oxadiazol-2-yl]-pyrrolidin-1-yl}-methanone
(2,6-difluoro-phenyl)-[2-(5-pyridin-4-yl-[1,3,4]oxadiazol-2-yl)-pyrrolidin-1-yl]-methanone
(4-ethoxy-phenyl)-[2-(5-phenyl-[1,3,4]oxadiazol-2-yl)-pyrrolidin-1-yl]-methanone
3-{5-[1-(4-trifluoromethoxy-benzylsulfonyl)-pyrrolidin-2-yl]-[1,3,4]oxadiazol-2-yl}-pyridine
(2,5-bis-trifluoromethyl-phenyl)-{2-[5-(4-chloro-phenyl)-[1,3,4]oxadiazol-2-yl]-pyrrolidin-1-yl}-methanone
(2,5-bis-trifluoromethyl-phenyl)-[2-(5-thiophen-2-yl-[1,3,4]oxadiazol-2-yl)-pyrrolidin-1-yl]-methanone
(1-phenyl-5-propyl-1H-pyrazol-4-yl)-[2-(5-pyridin-3-yl-[1,3,4]oxadiazol-2-yl)-pyrrolidin-1-yl]-methanone
(2,3-difluoro-phenyl)-{2-[5-(3-methoxy-phenyl)-[1,3,4]oxadiazol-2-yl]-pyrrolidin-1-yl}-methanone
(2-methyl-6-trifluoromethyl-pyridin-3-yl)-[2-(5-phenyl-[1,3,4]oxadiazol-2-yl)-pyrrolidin-1-yl]-methanone
[2-(5-phenyl-[1,3,4]oxadiazol-2-yl)-pyrrolidin-1-yl]-(4-trifluoromethylsulfanyl-phenyl)-methanone
2,2,2-trifluoro-1-{7-[2-(5-pyridin-4-yl-[1,3,4]oxadiazol-2-yl)-pyrrolidin-1sulfonyl]-3,4-dihydro-1H-isoquinolin-2-yl}-ethanone
1-{2-[5-(3-chloro-phenyl)-[1,3,4]oxadiazol-2-yl]-pyrrolidin-1-yl}-3-cyclopentyl-propan-1-one, and
1-{2-[5-(3-chloro-phenyl)-[1,3,4]oxadiazol-2-yl]-pyrrolidin-1-yl}-pentan-1-one The terms "alkyl", "C$_{1-10}$ alkyl", and "C$_{1-6}$ alkyl", according to this invention, include acyclic saturated or unsaturated hydrocarbon radicals, which may be branched or straight chained and unsubstituted or singly substituted or multiply identically or differently substituted, with (as in the case of C$_{1-10}$ alkyl) 1 to 10 (i.e. 1, 2, 3, 4, 5, 6, 7, 8, 9 or 10) or (as in the case of C$_{1-6}$ alkyl) 1 to 6 (i.e. 1, 2, 3, 4, 5 or 6), i.e. C$_{1-10}$, C$_{1-6}$ alkanyls, C$_{2-10}$, C$_{2-6}$ alkenyls and C$_{2-10}$, C$_{2-6}$ alkynyls. Alkenyls have at least one C—C double bond and alkynyls at least one C—C treble bond. Alkyl is advantageously selected from the group consisting of methyl, ethyl, n-propyl, 2-propyl, n-butyl, iso-butyl, sec.-butyl, tert-butyl, n-pentyl, iso-pentyl, neo-pentyl, n-hexyl, 2-hexyl, n-heptyl, n-octyl, n-nonyl, n-decyl; ethenyl (vinyl), ethynyl, propenyl (—CH$_2$CH=CH$_2$, —CH=CH—CH$_3$, —C(=CH$_2$)—CH$_3$), propynyl (—CH$_2$—C=CH, —C=C—CH$_3$), butenyl, butynyl, pentenyl, pentynyl, hexenyl, hexynyl, octenyl and octynyl. According to this invention "alkyl" is also taken to mean radicals in which the carbon atom chain is optionally interrupted by one or more of the heteroatoms N, O or S, preferably by O.

"$C_{3-10}$ cycloalkyl" (or "cycloalkyl"), according to this invention, denotes cyclic saturated or unsaturated hydrocarbon radicals with 3, 4, 5, 6, 7, 8, 9 or 10 carbon atoms, wherein each of the radicals may be unsubstituted or singly substituted or multiply identically or differently substituted and optionally benzo-condensed. A bi-, tri- or polycyclic ring system may also be involved. By way of example cycloalkyl represents cyclopropyl, cyclobutyl, cyclopentyl, cyclohexyl, cycloheptanyl and cyclooctanyl and adamantyl and bicyclo[2.2.1]heptyl.

For the purpose of the present invention, the term "aryl" denotes a radical which is selected from the group consisting of phenyl, naphthyl, phenanthrenyl, anthracenyl and biphenyl, and is unsubstituted or singly or multiply identically or differently substituted. Aryl is preferably an unsubstituted or singly substituted or multiply identically or differently substituted phenyl, 1-naphthyl or 2-naphthyl group.

The term "heterocyclyl" represents a monocyclic or polycyclic organic radical, in which at least one cycle contains 1 heteroatom or 2, 3, 4 or 5 identical or different heteroatoms, which is/are selected from the group consisting of N, O and S, the radical being saturated or unsaturated and unsubstituted or singly substituted or multiply identically or differently substituted. Examples of heterocyclyl radicals according to this invention include monocyclic five-, six- or seven-membered organic radicals with 1 heteroatom or 2, 3, 4 or 5 identical or different heteroatoms, wherein this/these is/are nitrogen, oxygen and/or sulfur, and the benzo-condensed analogues thereof. The "heteroaryl" radicals form a subgroup of the heterocyclyl radicals, these being heterocycles in which the at least one cycle, containing the heteroatom(s), is heteroaromatic. Each heteroaryl radical may be unsubstituted or singly substituted or multiply identically or differently substituted. Examples of heterocyclyl radicals according to the present invention include pyrrolidinyl, piperidinyl and morpholinyl. Examples of heteroaryl radicals include pyrrolyl, furanyl, thienyl, thiadiazolyl, triazolyl, isoxazolyl, isoquinoline, pyrazolyl, imidazolyl, pyridazinyl, pyrimidinyl, pyrazinyl, pyridinyl and oxadiazolyl and the benzo-condensed analogues thereof (e.g. benzooxadiazolyl). All of these radicals may be respectively unsubstituted or substituted.

For the purposes of the present invention, the terms "($C_{1-6}$ alkyl)-$C_{3-10}$ cycloalkyl" and "($C_{1-6}$ alkyl)-aryl" mean that the cycloalkyl or aryl radical is bound by a $C_{1-6}$ alkyl group to the compound substituted by it.

In connection with "alkyl", "alkanyl", "alkenyl", "alkynyl" and "cycloalkyl", the term "substituted" according to this invention denotes single or multiple substitution of one or more hydrogen atoms by for example F, Cl, Br, I, —CN, NH$_2$, NH-alkyl, NH-aryl, NH-alkyl-aryl, NH-heterocyclyl, N(alkyl)$_2$, N(alkyl-aryl)$_2$, N-alkyl-N-aryl, NO$_2$, OH, keto group, O-alkyl, O-aryl, O-alkyl-aryl, C(=O)C$_{1-6}$ alkyl, C(=O)aryl, C(=O)C$_{1-6}$ alkyl-aryl, C(=O)-heterocyclyl, CO$_2$H, CO$_2$-alkyl, CO$_2$-alkyl-aryl, C(=O)NH$_2$, C(=O)NH-alkyl, C(=O)NH-aryl, C(=O)NH-heterocyclyl, C(=O)N(alkyl)$_2$, C(=O)N(alkyl-aryl)$_2$, cycloalkyl, aryl or heterocyclyl, the multiple substitution taking place either multiply, for example doubly or triply, on different atoms or the same atoms. Multiple substitution may take place with the same substituent or with different substituents. Substitution is also possible with a sulfonamide.

With respect to "aryl", "heterocyclyl" and "heteroaryl", according to this invention, "substituted" is taken to mean single or multiple, e.g. double, triple or quadruple, substitution of one or more hydrogen atoms of the ring system by a suitable substituent. If the meaning of these suitable substituents in connection with "aryl", "heterocyclyl" or "heteroaryl" is not defined elsewhere in the description or in the claims, suitable substituents are F, Cl, Br, I, —CN, NH$_2$, NH-alkyl, NH-aryl, NH-alkyl-aryl, NH-heterocyclyl, N(alkyl)$_2$, N(alkyl-aryl)$_2$, NO$_2$, SH, S-alkyl, OH, O-alkyl, O-cycloalkyl, O-aryl, O-alkyl-aryl, O-heterocyclyl, CHO, C(=O)C$_{1-6}$ alkyl, C(=O)CF$_3$, C(=O)aryl, C(=O)—C$_{1-6}$ alkyl-aryl, CO$_2$H, CO$_2$-alkyl, -alkyl-CO$_2$-aryl, C(=O)NH$_2$, C(=O)NH-alkyl, C(=O)NH-aryl, C(=O)NH-heterocyclyl, C(=O)N(alkyl)$_2$, SO$_2$NH$_2$, SO$_3$H, CF$_3$, CHF$_2$, CH$_2$F, OCF$_3$, OCHF$_2$, OCH$_2$F, SCF$_3$, SCHF$_2$, alkyl, cycloalkyl, aryl and/or heterocyclyl; on one atom or optionally on different atoms (wherein a substituent may, in turn, optionally be substituted). Multiple substitution takes place here using the same or different substituents. Particularly preferred substituents for aryl and heterocyclyl are $C_{1-6}$ alkyl, F, Cl, Br, I, CF$_3$, O-alkyl, OCF$_3$, phenyl, CN and/or NO$_2$.

For the purposes of the present invention "benzo-condensed" means that a benzene ring is condensed onto a different cycle.

The invention also relates to a process for producing substituted 2-pyrrolidin-2-yl-[1,3,4]-oxadiazole compounds corresponding to formula I. The substances according to the invention are produced using the following synthesis pattern:

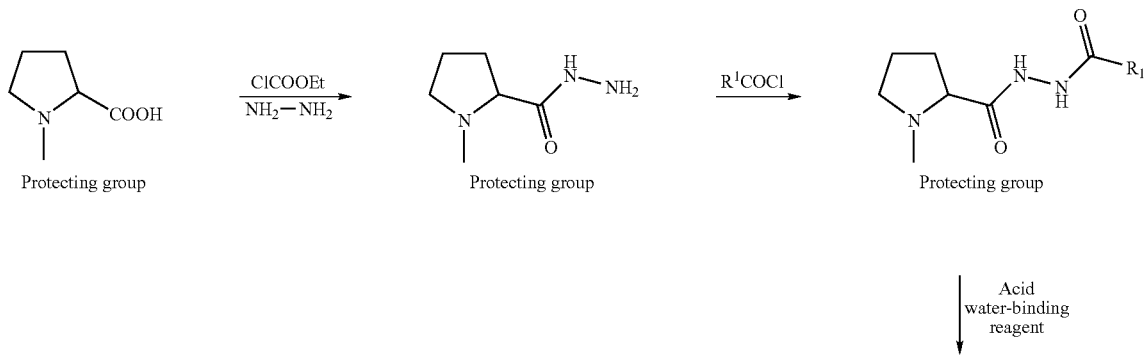

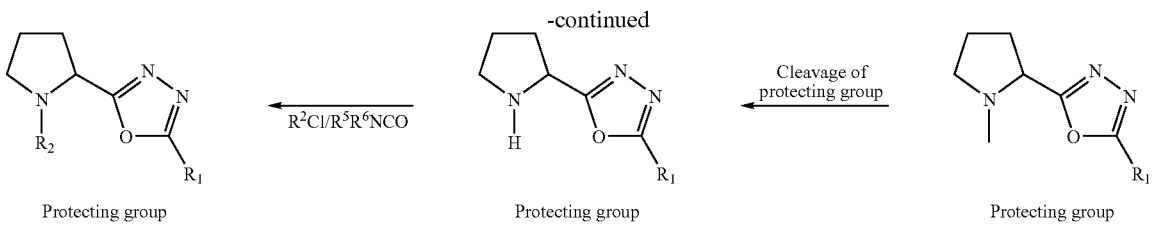

To produce the substituted 2-pyrrolidin-2-yl-[1,3,4]-oxadiazole derivatives according to the invention Boc-proline was reacted with ethyl chloroformate and hydrazine in a suitable solvent, for example THF (tetrahydrofuran). The resultant hydrazide was reacted with an acid chloride in a suitable solvent, for example THF, to form a diacylhydrazide. To close the ring, acid and a dehydrating reagent, for example $P_2O_5$, $CH_3SO_3H$, pyridine and/or $SOCl_2$, were added to the diacylhydrazide. Following ring closure, the protecting group was cleaved and the product reacted with an acid chloride or an isocyanate and the compounds according to the invention of general formula I were obtained.

The substituted 2-pyrrolidin-2-yl-[1,3,4]-oxadiazole derivatives according to the invention of general formula 1 are toxicologically safe and are therefore suitable as pharmaceutical active ingredients in pharmaceutical compositions. The present invention therefore also relates to pharmaceutical compositions which contain at least one substituted 2-pyrrolidin-2-yl-[1,3,4]-oxadiazole compound corresponding to formula I and optionally physiologically acceptable auxiliaries. The pharmaceutical compositions according to the invention are preferably suitable for combating pain and for the treatment or inhibition of depression, urinary incontinence, diarrhea, pruritus, alcohol, drug and or medicine dependency, nausea and vomiting, for anxiolysis, increasing alertness and/or increasing libido.

The present invention also relates to the use of at least one substituted 2-pyrrolidin-2-yl-[1,3,4]-oxadiazole compound corresponding to formula I for producing a pharmaceutical composition for combating pain and for the treatment or inhibition of depression, urinary incontinence, diarrhea, pruritus, alcohol, drug and or medicine dependency, nausea and vomiting, for anxiolysis, increasing alertness and/or for increasing libido. The invention also relates to a process for the treatment of depression, in which the compounds according to the invention are used.

The pharmaceutical compositions according to the invention may exist as liquid, semi-solid or solid pharmaceutical forms, for example in the form of injection solutions, drops, juices, syrups, sprays, suspensions, tablets, patches, capsules, plasters, suppositories, ointments, creams, lotions, gels, emulsions, aerosols or in multi-particulate form, for example in the form von pellets or granules, and may also be administered as such.

In addition to at least one substituted 2-pyrrolidin-2-yl-[1,3,4]-oxadiazole compound according to the invention corresponding to formula I the pharmaceutical compositions according to the invention conventionally contain further physiologically acceptable pharmaceutical auxiliaries, which are preferably selected from the group consisting of excipients, fillers, solvents, diluents, surface-active agents, dyes, preservatives, blasting agents, lubricants, flavorings and binders. The choice of physiologically acceptable auxiliaries and the amounts thereof to be used depend on whether the pharmaceutical composition is to be administered orally, subcutaneously, parenterally, intravenously, intraperitoneally, intradermally, intramuscularly, intranasally, buccally, rectally or topically, for example to infections of the skin, the mucous membranes or the eyes. Preparations in the form of tablets, dragées, capsules, granules, pellets, drops, juices and syrups are suitable for oral administration; solutions, suspensions, easily reconstitutable dry preparations and sprays are suitable for parenteral, topical and inhalative administration. Suitable percutaneous administration preparations include compounds according to the invention of general formula I in a depot, in dissolved form or in a plaster, optionally with the addition of agents to promote skin penetration. Orally or percutaneously applicable preparation forms may also release the compounds according to the invention of general formula I after a delay.

The pharmaceutical compositions according to the invention are produced using conventional means, devices methods and processes known to a person skilled in the art, as described for example in A. R. Gennaro (ed.), Remington's Pharmaceutical Sciences, 17$^{th}$ Edition, Mack Publishing Company, Easton, Pa. (1985), in particular in part 8, chapters 76 to 93. The corresponding description of the literature is incorporated herein by reference and forms part of this disclosure.

The amount of the respective compound according to the invention corresponding to formula I to be administered to the patient may vary and depends, for example, on the weight or age of the patient and on the method of administration, the indication and the severity of the disease. Conventionally 0.005 to 500 mg/kg, preferably 0.05 to 5 mg/kg body weight of the patient of at least one substituted 2-pyrrolidin-2-yl-[1,3,4]-oxadiazole derivative according to the invention of general formula I are administered.

While the compounds according to the invention fall under the comprehensive general formula of Japanese patent application no. JP 2001247569, they are not explicitly described therein, nor do they belong to the preferred compounds disclosed therein. The compounds described therein are said to be capable of lengthening nerve extensions and therefore suitable for the treatment and/or prevention of diseases such as diabetic nerve disorders, neuropathy, severed nerves, nerve-destroying diseases such as ALS or multiple sclerosis, Alzheimer's disease, Parkinson's disease, Huntington's chorea or spinal chord injuries.

In contrast thereto, the analgesically effective compounds according to the present invention have been shown to have a clear anti-depressive effect.

EXAMPLES

| Example no. | Compound according to the invention |
|---|---|
| 1 | 4-{5-[1-(4-nitro-benzylsulfonyl)-pyrrolidin-2-yl]-[1,3,4]oxadiazol-2-yl}-pyridine |
| 2 | 3-oxo-3-[2-(5-pyridin-3-yl-[1,3,4]oxadiazol-2-yl)-pyrrolidin-1-yl]-propanoic acid ethyl ester |
| 3 | 4-{5-1-(2,4,6-trimethyl-benzylsulfonyl)-pyrrolidin-2-yl]-[1,3,4]oxadiazol-2-yl}-pyridine |
| 4 | 4-oxo-4-[2-(5-pyridin-4-yl-[1,3,4]oxadiazol-2-yl)-pyrrolidin-1-yl]-butyric acid ethyl ester |
| 5 | (2,4-dimethoxy-phenyl)-[2-(5-pyridin-4-yl-[1,3,4]oxadiazol-2-yl)-pyrrolidin-1-yl]methanone |
| 6 | (2-chloro-pyridin-3-yl)-[2-(5-pyridin-4-yl-[1,3,4]oxadiazol-2-yl)pyrrolidin-1-yl]-methanone |
| 7 | 7,7-dimethyl-1-[2-(5-pyridin-4-yl-[1,3,4]oxadiazol-2-yl)-pyrrolidin-1-sulfonylmethyl]-bicyclo[2.2.1]heptan-2-one |
| 8 | 1-[2-(5-pyridyl-4-yl-[1,3,4]oxadiazol-2-yl)-pyrrolidin-1-yl]-butan-1-one |
| 9 | [2-(5-biphenyl-4-yl-[1,3,4]oxadiazol-2-yl)-pyrrolidin-1-yl]-(4-methoxy-phenyl)-methanone |
| 10 | 2-[1-(3-chloro-4-fluoro-benzylsulfonyl)-pyrrolidin-2-yl]-5-thiophen-2-yl-[1,3,4]oxadiazole |
| 11 | 3-(2,6-dichloro-phenyl)-5-methyl-isoxazol-4-yl]-[2-(5-pyridin-4-yl-[1,3,4]oxadiazol-2-yl)-pyrrolidin-1-yl]-methanone |
| 12 | (3-dimethyamino-phenyl)-[2-(5-pyridin-3-yl-[1,3,4]oxadiazol-2-yl)-pyrrolidin-1-yl]-methanone |
| 13 | 2-(3,4-dimethoxy-phenyl)-1-[2-(5-pyridin-4-yl-[1,3,4]oxadiazol-2-yl)-pyrrolidin-1-yl]-ethanone |
| 14 | [2-(5-biphenyl-4-yl-[1,3,4]oxadiazol-2-yl)-pyrrolidin-1-yl]-(4-chloro-phenyl)-methanone |
| 15 | 4-{5-[1-(4-chloro-benzylsulfonyl)-pyrrolidin-2-yl]-[1,3,4]oxadiazol-2-yl}-pyridine |
| 16 | 4-{5-[1-(4-methoxy-benzylsulfonyl)-pyrrolidin-2-yl]-[1,3,4]oxadiazol-2-yl}-pyridine |
| 17 | isoxazol-5-yl-[2-(5-pyridin-3-yl-[1,3,4]oxadiazol-2-yl)-pyrrolidin-1-yl]-methanone |
| 18 | 4-{5-[1-(butane-1-sulfonyl)-pyrrolidin-2-yl]-[1,3,4]oxadiazol-2-yl}-pyridine |
| 19 | 2-(2-methoxy-ethoxy)-1-{2-[5-(3-methoxy-phenyl)-[1,3,4]oxadiazol-2-yl]-pyrrolidin-1-yl}-ethanone |
| 20 | cyclobutyl-[2-(5-pyridin-3-yl-[1,3,4]oxadiazol-2-yl)-pyrrolidin-1-yl]-methanone |
| 21 | N-{1-benzyl-2-oxo-2-[2-(5-pyridin-4-yl-[1,3,4]oxadiazol-2-yl)-pyrrolidin-1-yl]-ethyl}-4-methyl-benzylsulfonamide |
| 22 | 4-{5-[1-(4,5-dichloro-thiophene-2-sulfonyl)-pyrrolidin-2-yl]-[1,3,4]oxadiazol-2-yl}-pyridine |
| 23 | 1-[2-(5-phenyl-[1,3,4]oxadiazol-2-yl)-pyrrolidin-1-yl]-ethanone |
| 24 | 1-{2-[5-(2-fluoro-phenyl)-[1,3,4]oxadiazol-2-yl]-pyrrolidin-1-yl}-2-methoxy-ethanone |
| 25 | (2-chloro-pyridin-4-yl)-[2-(5-pyridin-3-yl-[1,3,4]oxadiazol-2-yl)-pyrrolidin-1-yl]-methanone |
| 26 | [2-(5-pyridin-4-yl-[1,3,4]oxadiazol-2-yl)-pyrrolidin-1-yl]-(3,4,5-trimethoxy-phenyl)-methanone |
| 27 | (4-bromo-phenyl)-{2-[5-(4-chloro-phenyl)-[1,3,4]oxadiazol-2-yl]-pyrrolidin-1-y)}-methanone |
| 28 | 5-{2-[5-(2-fluoro-phenyl)-[1,3,4]oxadiazol-2-yl]-pyrrolidin-1-yl}-5-oxo-valeric acid methyl ester |
| 29 | [2-(5-biphenyl-4-yl-[1,3,4]oxadiazol-2-yl)-pyrrolidin-1-yl]-[3-(2-chloro-phenyl)-5-methyl-isoxazol-4-yl]-methanone |
| 30 | 3-{5-[1-(2,5-dimethoxyl-benzylsulfonyl)-pyrrolidin-2-yl]-[1,3,4]oxadiazol-2-yl}-pyridine |
| 31 | (2-methylsulfanyl-pyridin-3-yl)-[2-(5-pyridin-3-yl-[1,3,4]oxadiazol-2-yl)-pyrrolidin-1-yl]-methanone |
| 32 | 2-phenyl-1-[2-(5-pyridin-4-yl-[1,3,4]oxadiazol-2-yl)-pyrrolidin-1-yl]-ethanone |
| 33 | 3-oxo-3-[2-(5-thiophen-2-yl-[1,3,4]oxadiazol-2-yl)-pyrrolidin-1-yl]-propanoic acid ethyl ester |
| 34 | (3-dimethylamino-phenyl)-{2-[5-(3-methoxy-phenyl)-[1,3,4]oxadiazol-2-yl]-pyrrolidin-1-yl}-methanone |
| 35 | acetic acid 2-oxo-2-[2-(5-phenyl-[1,3,4]oxadiazol-2-yl)-pyrrolidin-1-yl]-ethyl ester |
| 36 | (4-ethoxy-phenyl)-[2-(5-pyridin-3-yl-[1,3,4]oxadiazol-2-yl)-pyrrolidin-1-yl]-methanone |
| 37 | 2-(2,5-dimethoxy-phenyl)-1-[2-(5-pyridin-4-yl-[1,3,4]oxadiazol-2-yl)-pyrrolidin-1-yl]-ethanone |
| 38 | 3-oxo-3-[2-(5-thiophen-2-yl-[1,3,4]oxadiazol-2-yl)-pyrrolidin-1-yl]-propanoic acid methyl ester |
| 39 | (2-ethoxy-phenyl)-[2-(5-pyridin-4-yl-[1,3,4]oxadiazol-2-yl)-pyrrolidin-1-yl]-methanone |
| 40 | 3-[5-(1-phenylmethane sulfonyl-pyrrolidin-2-yl)-[1,3,4]oxadiazol-2-yl]-pyridine |
| 41 | 2-(5-pyridin-4-yl-[1,3,4]oxadiazol-2-yl)-pyrrolidin-1-sulfonic acid dimethylamide |
| 42 | 4,7,7-trimethyl-1-[2-(5-phenyl-[1,3,4]oxadiazol-2-yl)-pyrrolidin-1-carbonyl]-2-oxa-bicyclo[2.2.1]heptan-3-one |
| 43 | {2-[5-(3-methoxy-phenyl)-[1,3,4]oxadiazol-2-yl)-pyrrolidin-1-yl]-(4-trifluoromethoxy-phenyl)-methanone |
| 44 | [2-(5-pyridin-4-yl-[1,3,4]oxadiazol-2-yl)-pyrrolidin-1-yl]-thiophen-2-yl-methanone |
| 45 | [2-(5-pyridin-4-yl-[1,3,4]oxadiazol-2-yl)-pyrrolidin-1-yl]-o-tolyl-methanone |
| 46 | 1-{2-[5-(4-chloro-phenyl)-[1,3,4]oxadiazol-2-yl]-pyrrolidin-1-yl}-2-methoxy-ethanone |
| 47 | 5-{2-[5-(3-methoxy-phenyl)-[1,3,4]oxadiazol-2-yl]-pyrrolidin-1-yl}-5-oxo-valeric acid methyl ester |
| 48 | 3-{2-[5-(3-methoxy-phenyl)-[1,3,4]oxadiazol-2-yl]-pyrrolidin-1-yl}-3-oxo-propanoic acid methyl ester |
| 49 | biphenyl-4-yl-[2-(5-phenyl-[1,3,4]oxadiazol-2-yl)-pyrrolidin-1-yl]-methanone |
| 50 | (2-chloro-phenyl)-[2-(5-pyridin-4-yl-[1,3,4]oxadiazol-2-yl)-pyrrolidin-1-yl]-methanone |
| 51 | (2-chloro-pyridin-3-yl)-[2-(5-thiophen-2-yl-[1,3,4]oxadiazol-2-yl)-pyrrolidin-1-yl]-methanone |
| 52 | 1-[2-(5-thiophen-2-yl-[1,3,4]oxadiazol-2-yl)-pyrrolidin-1-yl]-butan-1-one |
| 53 | acetic acid 1,1-dimethyl-2-oxo-2-[2-(5-phenyl-[1,3,4]oxadiazol-2-yl)-pyrrolidin-1-yl]-ethyl ester |
| 54 | [2-(5-pyridin-4-yl-[1,3,4]oxadiazol-2-yl)-pyrrolidin-1-yl]-p-tolyl-methanone |
| 55 | (2,3-dimethyl-phenyl)-[2-(5-pyridin-3-yl-[1,3,4]oxadiazol-2-yl)-pyrrolidin-1-yl]-methanone |
| 56 | 2-cyclopentyl-1-[2-(5-pyridin-4-yl-[1,3,4]oxadiazol-2-yl)-pyrrolidin-1-yl]-ethanone |
| 57 | 3-{5-[1-(3-chloro-benzylsulfonyl)-pyrrolidin-2-yl]-[1,3,4]oxadiazol-2-yl}-pyridine |
| 58 | 1-{2-[5-(3-methoxy-phenyl)-[1,3,4]oxadiazol-2-yl]-1-yl-}-pentan-1-one |
| 59 | 1-{2-[5-(3-methoxy-phenyl)-[1,3,4]oxadiazol-2-yl]-pyrrolidin-1-carbonyl]-4,7,7-trimethyl-2-oxa-bicyclo[2.2.1]heptan-3-one |
| 60 | adamantan-1-yl-[2-(5-pyridin-3-yl-[1,3,4]oxadiazol-2-yl)-pyrrolidin-1-yl]-methanone |
| 61 | 2-(2-fluoro-phenyl)-5-[1-(2,4,6-trimethyl-benzylsulfonyl)-pyrrolidin-2-yl]-[1,3,4]oxadiazole |
| 62 | [2-(5-pyridin-4-yl-[1,3,4]oxadiazol-2-yl)-pyrrolidin-1-yl]-(2-trifluoromethyl-phenyl)-methanone |
| 63 | 2-[1-(3,4-dimethoxy-benzylsulfonyl)-pyrrolidin-2-yl]-5-(2-fluoro-phenyl)-[1,3,4]oxadiazole |
| 64 | acetic acid 2-oxo-1-phenyl-2-[2-(5-pyridin-3-yl-[1,3,4]oxadiazol-2-yl)-pyrrolidin-1-yl]-ethyl ester |
| 65 | furan-2-yl-{2-[5-(3-methoxy-phenyl)-[1,3,4]oxadiazol-2-yl]-pyrrolidin-1-yl}-methanone |
| 66 | (4-bromo-phenyl)-[2-(5-pyridin-3-yl-[1,3,4]oxadiazol-2-yl)-pyrrolidin-1-yl]-methanone |
| 67 | 2-(4-chloro-phenoxy)-1-[2-(5-pyridin-4-yl-[1,3,4]oxadiazol-2-yl)-pyrrolidin-1-yl]-ethanone |
| 68 | 4-[5-(1-benzylsulfonyl-pyrrolidin-2-yl)-[1,3,4]oxadiazol-2-yl]-pyridine |
| 69 | furan-2-yl-[2-(5-thiophen-2-yl-[1,3,4]oxadiazol-2-yl)-pyrrolidin-1-yl]-methanone |
| 70 | 1-{2-[5-(2-fluoro-phenyl)-[1,3,4]oxadiazol-2-yl]-pyrrolidin-1-yl}-pent-4-en-1-one |
| 71 | 3-{5-[1-(2-chloro-benzylsulfonyl)-pyrrolidin-2-yl]-[1,3,4]oxadiazol-2-yl}-pyridine |
| 72 | 4-{5-[1-(5-chloro-thiophen-2-sulfonyl)-pyrrolidin-2-yl]-[1,3,4]oxadiazol-2-yl}-pyridine |
| 73 | [3-(2-chloro-phenyl)-5-methyl-isoxazol-4-yl]-[2-(5-pyridin-3-yl-[1,3,4]oxadiazol-2yl)-pyrrolidin-1-yl]-methanone |
| 74 | (5-methyl-isoxazol-3-yl)-[2-(5-pyridin-3-yl-[1,3,4]oxadiazol-2-yl)-pyrrolidin-1-yl]-methanone |

| Example no. | Compound according to the invention |
|---|---|
| 75 | {2-[5-(2-fluoro-phenyl)-[1,3,4]oxadiazol-2-yl]-pyrrolidin-1-yl}-pentafluorophenyl-methanone |
| 76 | 4-oxo-4-[2-(5-thiophen-2-yl-[1,3,4]oxadiazol-2-yl)-pyrrolidin-1-yl]-butyric acid ethyl ester |
| 77 | 2-(3-methoxy-phenyl)-5-[1-(4-methoxy-2,3,6-trimethyl-benzylsulfonyl)-pyrrolidin-2-yl]-[1,3,4]oxadiazole |
| 78 | 4-{5-[1-(2,3,5,6-tetramethyl-benzylsulfonyl)-pyrrolidin-2-yl]-[1,3,4]oxadiazol-2-yl}-pyridine |
| 79 | 1-[2-(5-pyridin-4-yl-[1,3,4]oxadiazol-2yl)-pyrrolidin-1-yl]-hexan-1-one |
| 80 | cyclopentyl-[2-(5-pyridin-4-yl-[1,3,4]oxadiazol-2-yl)-pyrrolidin-1-yl]-methanone |
| 81 | (3-chloro-2-fluoro-phenyl)-{2-[5-(2-fluoro-phenyl)-[1,3,4]oxadiazol-2-yl]-pyrrolidin-1-yl}methanone |
| 82 | 2-[1-(4-chloro-2,5-dimethoxy-benzylsulfonyl)-pyrrolidin-2-yl]-5-(4-chloro-phenyl)-[1,3,4]oxadiazole |
| 83 | (4-chloro-phenyl)-[2-(5-pyridin-3-yl-[1,3,4]oxadiazol-2-yl)-pyrrolidin-1-yl]-methanone |
| 84 | 3-phenyl-1-[2-(5-phenyl-[1,3,4]oxadiazol-2-yl)-pyrrolidin-1-yl]-propenone |
| 85 | (5-methyl-2-phenyl-[1,2,3] triazol-4-yl)-[2-(5-pyridin-4-yl-[1,3,4]oxadiazol-2-yl)-pyrrolidin-1-yl]-methanone |
| 86 | 3-{5-[1-(2,4-difluoro-benzylsulfonyl)-pyrrolidin-2-yl]-[1,3,4]oxadiazol-2-yl}-pyridine |
| 87 | 2-benzyloxy-1-{2-[5-(3-methoxy-phenyl)-[1,3,4]oxadiazol-2-yl]-pyrrolidin-1-yl}-ethanone |
| 88 | (6-chloro-pyridin-3-yl)-[2-(5-thiophen-2-yl-[1,3,4]oxadiazol-2-yl)-pyrrolidin-1-yl]-methanone |
| 89 | 3,3-dimethyl-1-[2-(5-thiophen-2-yl-[1,3,4]oxadiazol-2-yl)-pyrrolidin-1-yl]-butan-1-one |
| 90 | (2-ethoxy-phenyl)-{2-[5-(3-methoxy-phenyl)-[1,3,4]oxadiazol-2-yl]-pyrrolidin-1-yl}-methanone |
| 91 | (4-ethyl-phenyl)-[2-(5-pyridin-4-yl-[1,3,4]oxadiazol-2-yl)-pyrrolidin-1-yl]-methanone |
| 92 | (4-bromo-phenyl)-{2-[5-(3-methoxy-phenyl)-[1,3,4]oxadiazol-2-yl]-pyrrolidin-1-yl}-methanone |
| 93 | (5-methyl-isoxazol-3-yl)-[2-(5-phenyl-[1,3,4]oxadiazol-2-yl)-pyrrolidin-1-yl]-methanone |
| 94 | (2-chloro-pyridin-4-yl)-{2-[5-(3-methoxy-phenyl)-[1,3,4]oxadiazol-2-yl]-pyrrolidin-1-yl}-methanone |
| 95 | {2-[5-(2-fluoro-phenyl)-[1,3,4]oxadiazol-2-yl]-pyrrolidin-1-yl}-(4-nitro-phenyl)-methanone |
| 96 | 1-{2-[5-(3-methoxy-phenyl)-[1,3,4]oxadiazol-2-yl]-pyrrolidin-1-yl}-3-phenyl-propan-1-one |
| 97 | (3-chloro-thiophen-2-yl)-{2-[5-(3-methoxy-phenyl)-[1,3,4]oxadiazol-2-yl]-pyrrolidin-1-yl}-methanone |
| 98 | 2-(2-fluoro-phenyl)-5-[1-(toluene-4-sulfonyl)-pyrrolidin-2-yl]-[1,3,4]oxadiazole |
| 99 | 4-{5-[1-(4-butoxy-benzylsulfonyl)-pyrrolidin-2-yl]-[1,3,4]oxadiazol-2-yl}-pyridine |
| 100 | cyclopropyl-[2-(5-phenyl-[1,3,4]oxadiazol-2-yl)-pyrrolidin-1-yl]-methanone |
| 101 | (2,6-difluoro-phenyl)-[2-(5-pyridin-4-yl-[1,3,4]oxadiazol-2-yl)-pyrrolidin-1-yl]-methanone |
| 102 | (2,5-dimethyl-furan-3-yl)-[2-(5-pyridin-4-yl-[1,3,4]oxadiazol-2-yl)-pyrrolidin-1-yl]-methanone |
| 103 | 2-[2-(5-pyridin-3-yl-[1,3,4]oxadiazol-2-yl)-pyrrolidin-1-sulfonyl]-methyl benzoate |
| 104 | 2-ethyl-1-[2-(5-thiophen-2-yl-[1,3,4]oxadiazol-2-yl)-pyrrolidin-1-yl]-butan-1-one |
| 105 | (3-difluoromethylsulfanyl-phenyl)-[2-(5-pyridin-4-yl-[1,3,4]oxadiazol-2-yl)-pyrrolidin-1-yl]-methane |
| 106 | benzo[1,2,5]oxadiazol-5-yl-{2-[5-(3-methoxy-phenyl)-[1,3,4]oxadiazol-2-yl]-pyrrolidin-1-yl}-methanone |
| 107 | 3-{5-[1-(toluene-4-sulfonyl)-pyrrolidin-2-yl]-[1,3,4]oxadiazol-2-yl}-pyridine |
| 108 | 4-{5-[1-(3-trifluoromethyl-benzylsulfonyl)-pyrrolidin-2-yl]-[1,3,4]oxadiazol-2-yl}-pyridine |
| 109 | (4-ethoxy-phenyl)-[2-(5-phenyl-[1,3,4]oxadiazol-2-yl)-pyrrolidin-1-yl]-methanone |
| 110 | 2-(2-bromo-phenyl)-1-[2-(5-pyridin-4-yl-[1,3,4]oxadiazol-2-yl)-pyrrolidin-1-yl]-ethanone |
| 111 | [2-(5-pyridin-4-yl-[1,3,4]oxadiazol-2-yl)-pyrrolidin-1-yl]-(4-trifluoromethyl-phenyl)-methanone |
| 112 | 2-thiophen-2-yl-5-[1-(2,4,6-trimethyl-benzylsulfonyl)-pyrrolidin-2-yl]-[1,3,4]oxadiazole |
| 113 | 1-{4-[2-(5-phenyl-[1,3,4]oxadiazol-2-yl)-pyrrolidin-1-sulfonyl]-phenyl}-ethanone |
| 114 | furan-2-yl-[2-(5-phenyl)-[1,3,4]oxadiazol-2-yl)-pyrrolidin-1-yl]-methanone |
| 115 | (3,5-difluoro-phenyl)-[2-(5-pyridin-4-yl-[1,3,4]oxadiazol-2-yl)-pyrrolidin-1-yl]-methanone |
| 116 | [2-(5-biphenyl-4-yl-[1,3,4]oxadiazol-2-yl)-pyrrolidin-1-yl]-(4-nitro-phenyl)-methanone |
| 117 | (4-fluoro-phenyl)-{2-[5-(2-fluoro-phenyl)-[1,3,4]oxadiazol-2-yl]-pyrrolidin-1-yl}-methanone |
| 118 | {2-[5-(3-methoxy-phenyl)-[1,3,4]oxadiazol-2-yl]-pyrrolidin-1-yl}-(4-propyl-phenyl)-methanone |
| 119 | (3,4-difluoro-phenyl)-[2-(5-pyridin-4-yl-[1,3,4]oxadiazol-2-yl)-pyrrolidin-1-yl]-methanone |
| 120 | (5-fluoro-2-trifluoromethyl-phenyl)-[2-(5-pyridin-4-yl-[1,3,4]oxadiazol-2-yl)-pyrrolidin-1-yl]-methanone |
| 121 | 2-phenyl-1-[2-(5-phenyl-[1,3,4]oxadiazol-2-yl)-pyrrolidin-1-yl]-ethanone |
| 122 | [2-(5-pyridin-3-yl-[1,3,4]oxadiazol-2-yl)-pyrrolidin-1-yl]-(3-trifluoromethoxy-phenyl)-methanone |
| 123 | (4-fluoro-phenyl)-{2-[5-(3-methoxy-phenyl)-[1,3,4]oxadiazol-2-yl]-pyrrolidin-1-yl}-methanone |
| 124 | (4-propyl-phenyl)-[2-(5-pyridin-4-yl-[1,3,4]oxadiazol-2-yl)-pyrrolidin-1-yl]-methanone |
| 125 | 2-phenyl-1-[2-(5-phenyl-[1,3,4]oxadiazol-2-yl)-pyrrolidin-1-yl]-butan-1-one |
| 126 | [2-(5-phenyl-[1,3,4]oxadiazol-2-yl)-pyrrolidin-1-yl]-(4-trifluoromethoxy-phenyl)-methanone |
| 127 | (3-nitro-phenyl)-[2-(5-pyridin-4-yl-[1,3,4]oxadiazol-2-yl)-pyrrolidin-1-yl]-methanone |
| 128 | 2-ethyl-1-{2-[5-(2-fluoro-phenyl)-[1,3,4]oxadiazol-2-yl]-pyrrolidin-1-yl}-butanone |
| 129 | (5-fluoro-2-trifluoromethyl-phenyl)-[2-(5-phenyl-[1,3,4]oxadiazol-2-yl)-pyrrolidin-1-yl]-methanone |
| 130 | 1-(2-[5-(2-fluoro-phenyl)-[1,3,4]oxadiazol-2-yl]-pyrrolidin-yl]-2-propyl-pentan-1-one |
| 131 | {2-[5-(3-methoxy-phenyl)-[1,3,4]oxadiazol-2-yl]-pyrrolidin-1-yl}-(5-methyl-2-phenyl-2H-[1,2,3]triazol-4-yl)-methanone |
| 132 | [2-(5-phenyl-[1,3,4]oxadiazol-2-yl)-pyrrolidin-1-yl]-(2-trifluoromethyl-phenyl)-methanone |
| 133 | 2-(3-methoxy-phenyl)-1-[2-(5-phenyl-[1,3,4]oxadiazol-2-yl)-pyrrolidin-1-yl]-ethanone |
| 134 | 3-{5-[1-(4-trifluoromethoxy-benzylsulfonyl)-pyrrolidin-2-yl]-[1,3,4]oxadiazol-2-yl}-pyridine |
| 135 | {2-[5-(4-chloro-phenyl)-[1,3,4]oxadiazol-2-yl]-pyrrolidin-1-yl}-furan-2-yl-methanone |
| 136 | {2-[5-(2-fluoro-phenyl)-[1,3,4]oxadiazol-2-yl]-pyrrolidin-1-yl}-furan-2-yl-methanone |
| 137 | (4-methyl-3-nitro-phenyl)-[2-(5-pyridin-4-yl-[1,3,4]oxadiazol-2-yl)-pyrrolidin-1-yl]-methanone |
| 138 | (4-methoxy-phenyl)-[2-(5-phenyl-[1,3,4]oxadiazol-2-yl)-pyrrolidin-1-yl]-methanone |
| 139 | (2-chloro-pyridin-4-yl)-{2-[5-(2-fluoro-phenyl)-[1,3,4]oxadiazol-2-yl]-pyrrolidin-1-yl}-methanone |
| 140 | (3-bromo-phenyl)-[2-(5-phenyl-[1,3,4]oxadiazol-2-yl)-pyrrolidin-1-yl]-methanone |
| 141 | 2-propyl-1-[2-(5-pyridin-3-yl-[1,3,4]oxadiazol-2-yl)-pyrrolidin-1-yl]-pentan-1-one |
| 142 | 2-(4-chloro-phenyl)-5-{1-[4-(1,1-dimethyl-propyl)-benzylsulfonyl]-pyrrolidin-2-yl-[1,3,4]oxadiazole |
| 143 | (3-chloro-phenyl)-[2-(5-pyridin-3-yl-[1,3,4]oxadiazol-2-yl)-pyrrolidin-1-yl]-methanone |
| 144 | (3-chloro-4-fluoro-phenyl)-[2-(5-pyridin-3-yl-[1,3,4]oxadiazol-2-yl)-pyrrolidin-1-yl]-methanone |
| 145 | (2,6-difluoro-3-methyl-phenyl)-[2-(5-pyridin-4-yl-[1,3,4]oxadiazol-2-yl)-pyrrolidin-1-yl]-methanone |
| 146 | (3-fluoro-4-methyl-phenyl)-{2-[5-(3-methoxy-phenyl)-[1,3,4]oxadiazol-2-yl]-pyrrolidin-1-yl}-methanone |
| 147 | {2-[5-(2-fluoro-phenyl)-[1,3,4]oxadiazol-2-yl]-pyrrolidin-1-yl}-(4-methyl-[1,2,3] thiadiazol-5-yl)-methanone |
| 148 | 2-thiophen-2-yl-5-[1-(toluene-4-sulfonyl)-pyrrolidin-2-yl]-[1,3,4]oxadiazole |
| 149 | {2-[5-(4-chloro-phenyl)-[1,3,4]oxadiazol-2-yl]-pyrrolidin-1-yl}-(3,4-dimethoxy-phenyl)-methanone |
| 150 | {2-[5-(4-chloro-phenyl)-[1,3,4]oxadiazol-2-yl]-pyrrolidin-1-yl}-(4-ethyl-phenyl)-methanone |

| Example no. | Compound according to the invention |
|---|---|
| 151 | (4-tert-butyl-phenyl)-[2-(5-phenyl-[1,3,4]oxadiazol-2-yl)-pyrrolidin-1-yl]-methanone |
| 152 | naphth-1-yl-[2-(5-phenyl-[1,3,4]oxadiazol-2-yl)-pyrrolidin-1-yl]-methanone |
| 153 | 1-[2-(5-phenyl-[1,3,4]oxadiazol-2-yl)-pyrrolidin-1-yl]-pent-4-en-1-one |
| 154 | {2-[5-(2-fluoro-phenyl)-[1,3,4]oxadiazol-2-yl]-pyrrolidin-1-yl}-(4-propyl-phenyl)-methanone |
| 155 | 1-{2-[5-(2-fluoro-phenyl)-[1,3,4]oxadiazol-2-yl]-pyrrolidin-1-yl}-3-phenyl-propenone |
| 156 | 1-{2-[5-(4-chloro-phenyl)-[1,3,4]oxadiazol-2-yl]-pyrrolidin-1-yl}-3,3-dimethyl-butan-1-one |
| 157 | 2-[1-(4-chloro-benzylsulfonyl)-pyrrolidin-2-yl]-5-(4-chloro-phenyl)-[1,3,4]oxadiazole |
| 158 | adamantan-1-yl-[2-(5-phenyl-[1,3,4]oxadiazol-2-yl)-pyrrolidin-1-yl]-methanone |
| 159 | {2-[5-(2-fluoro-phenyl)-[1,3,4]oxadiazol-2-yl]-pyrrolidin-1-yl}-o-tolyl-methanone |
| 160 | benzo[1,2,5]oxadiazol-5-yl-[2-(5-phenyl-[1,3,4]oxadiazol-2-yl)-pyrrolidin-1-yl]-methanone |
| 161 | (4-nitro-phenyl)-[2-(5-phenyl-[1,3,4]oxadiazol-2-yl)-pyrrolidin-1-yl]-methanone |
| 162 | 3-(2-chloro-phenyl)-1-{2-[5-(2-fluoro-phenyl)-[1,3,4]oxadiazol-2-yl]-pyrrolidin-1-yl}-propenone |
| 163 | 4-{5-[1-(4-ethyl-benzylsulfonyl)-pyrrolidin-2-yl]-[1,3,4]oxadiazol-2-yl}-pyridine |
| 164 | (2,5-bis-trifluoromethyl-phenyl)-{2-[5-(4-chloro-phenyl)-[1,3,4]oxadiazol-2-yl]-pyrrolidin-1-yl}-methanone |
| 165 | (2,5-bis-trifluoromethyl-phenyl)-[2-(5-thiophen-2-yl-[1,3,4]oxadiazol-2-yl)-pyrrolidin-1-yl]-methanone |
| 166 | (1-phenyl-5-propyl-1H-pyrazol-4-yl)-[2-(5-pyridin-3-yl-[1,3,4]oxadiazol-2-yl)-pyrrolidin-1-yl]-methanone |
| 167 | 1-[2-(5-pyridin-4-yl-[1,3,4]oxadiazol-2-yl)-pyrrolidin-1-yl]-3-(3-trifluoromethyl-phenyl)-propenone |
| 168 | (2-methylsulfanyl-pyridin-3-yl)-[2-(5-thiophen-2-yl-[1,3,4]oxadiazol-2-yl)-pyrrolidin-1-yl]-methanone |
| 169 | (2,5-dimethyl-furan-3-yl)-{2-[5-(3-methoxy-phenyl)-[1,3,4]oxadiazol-2-yl]-pyrrolidin-1-yl}-methanone |
| 170 | {2-[5-(4-chloro-phenyl)-[1,3,4]oxadiazol-2-yl]-pyrrolidin-1-yl}-(5-fluoro-2-trifluoromethyl-phenyl)-methanone |
| 171 | (3-chloro-phenyl)-[2-(5-thiophen-2-yl-[1,3,4]oxadiazol-2-yl)-pyrrolidin-1-yl]-methanone |
| 172 | (4-chloro-phenyl)-[2-(5-thiophen-2-yl-[1,3,4]oxadiazol-2-yl)-pyrrolidin-1-yl]-methanone |
| 173 | (2,3-difluoro-phenyl)-{2-[5-(3-methoxy-phenyl)-[1,3,4]oxadiazol-2-yl]-pyrrolidin-1-yl}-methanone |
| 174 | (2-methyl-6-trifluoromethyl-pyridin-3-yl)-[2-(5-phenyl-[1,3,4]oxadiazol-2-yl)-pyrrolidin-1-yl]-methanone |
| 175 | 1-{2-[5-(4-chloro-phenyl)-[1,3,4]oxadiazol-2-yl]-pyrrolidin-1-yl}-2-ethyl-butan-1-one |
| 176 | 1-{2-[5-(2-fluoro-phenyl)-[1,3,4]oxadiazol-2-yl]-pyrrolidin-1-yl}-pent-4-en-1-one |
| 177 | [2-(5-biphenyl-4-yl-[1,3,4]oxadiazol-2-yl)-pyrrolidin-1-yl]-pentafluorophenyl-methanone |
| 178 | (3-fluoro-4-trifluoromethyl-phenyl)-[2-(5-thiophen-2-yl-[1,3,4]oxadiazol-2-yl)-pyrrolidin-1-yl]-methanone |
| 179 | 1-{2-[5-(2-fluoro-phenyl)-[1,3,4]oxadiazol-2-yl]-pyrrolidin-1-yl}-4-phenoxy-butan-1-one |
| 180 | [1-(4-chloro-phenyl)-5-trifluoromethyl1H-pyrazol-4-yl]-{2-[5-(2-fluoro-phenyl)-[1,3,4]oxadiazol-2-yl]-pyrrolidin-1-yl}-methanone |
| 181 | [2-(5-phenyl-[1,3,4]oxadiazol-2-yl)-pyrrolidin-1-yl]-(4-trifluoromethylsulfanyl-phenyl)-methanone |
| 182 | 2,2,2-trifluoro-1-{7-[2-(5-pyridin-4-yl-[1,3,4]oxadiazol-2-yl)-pyrrolidin-1-sulfonyl]-3,4-dihydro-1H-isoquinolin-2-yl}-ethanone |
| 183 | 1-[2-(5-biphenyl-4-yl-[1,3,4]oxadiazol-2-yl)-pyrrolidin-1-yl]-2-methoxy-ethanone |
| 184 | (2-chloro-5-trifluoromethyl-phenyl)-[2-(5-pyridin-4-yl-[1,3,4]oxadiazol-2-yl)-pyrrolidin-1-yl]-methanone |
| 185 | (2-chloro-5-trifluoromethyl-phenyl)-[2-(5-phenyl-[1,3,4]oxadiazol-2-yl)-pyrrolidin-1-yl]-methanone |
| 186 | 1-{2-[5-(4-chloro-phenyl)-[1,3,4]oxadiazol-2-yl]-pyrrolidin-1-yl}-2-phenoxy-ethanone |
| 187 | (2,3-difluoro-4-methyl-phenyl)-{2-[5-(3-methoxy-phenyl)-[1,3,4]oxadiazol-2-yl]-pyrrolidin-1-yl}-methanone |
| 188 | 2-[2-(5-phenyl-[1,3,4]oxadiazol-2-yl)-pyrrolidin-1-sulfonyl]-methyl benzoate |
| 189 | 2-biphenyl-4-yl-5-{1-[4-(1,1-dimethyl-propyl)-benzylsulfonyl]-pyrrolidin-2-yl}-[1,3,4]oxadiazole |
| 190 | 3-cyclopentyl-1-[2-(5-phenyl-[1,3,4]oxadiazol-2-yl)-pyrrolidin-1-yl]-propan-1-one |
| 191 | 3,3-dimethyl-1-[2-(5-phenyl-[1,3,4]oxadiazol-2-yl)-pyrrolidin-1-yl]-butan-1-one |
| 192 | (2-chloro-4-nitro-phenyl)-[2-(5-phenyl-[1,3,4]oxadiazol-2-yl)-pyrrolidin-1-yl]-methanone |
| 193 | 1-[2-(5-biphenyl-4-yl-[1,3,4]oxadiazol-2-yl)-pyrrolidin-1-yl]-2-(2-methoxy-ethoxy)-ethanone |
| 194 | 1-{2-[5-(4-chloro-phenyl)-[1,3,4]oxadiazol-2-yl]-pyrrolidin-1-yl}-2-ethyl-hexan-1-one |
| 195 | 1-[2-(5-biphenyl-4-yl-[1,3,4]oxadiazol-2-yl)-pyrrolidin-1-yl]-2-phenyl-butan-1-one |
| 196 | (2,3-dimethyl-phenyl)-{2-[5-(2-fluoro-phenyl)-[1,3,4]oxadiazol-2-yl]-pyrrolidin-1-yl}-methanone |
| 197 | (2,5-bis-trifluoromethyl-phenyl)-[2-(5-pyridin-4-yl-[1,3,4]oxadiazol-2-yl)-pyrrolidin-1-yl]-methanone |
| 198 | 2-(4-chloro-phenoxy)-1-[2-(5-phenyl-[1,3,4]oxadiazol-2-yl)-pyrrolidin-1-yl]-ethanone |
| 199 | (2-ethoxy-phenyl)-[2-(5-phenyl-[1,3,4]oxadiazol-2-yl)-pyrrolidin-1-yl]-methanone |
| 200 | (5-tert-butyl-2-methyl-2H-pyrazol-3-yl)-[2-(5-phenyl-[1,3,4]oxadiazol-2-yl)-pyrrolidin-1-yl]-methanone |
| 201 | (4-methyl-[1,2,3]thiadiazol-5-yl)-[2-(5-thiophen-2-yl-[1,3,4]oxadiazol-2-yl)-pyrrolidin-1-yl]-methanone |
| 202 | [2-(5-biphenyl-4-yl-[1,3,4]oxadiazol-2-yl)-pyrrolidin-1-yl]-(3,4-dichloro-phenyl)-methanone |
| 203 | (4-propyl-phenyl)-[2-(5-thiophen-2-yl-[1,3,4]oxadiazol-2-yl)-pyrrolidin-1-yl]-methanone |
| 204 | (3,4-difluoro-phenyl)-[2-(5-phenyl-[1,3,4]oxadiazol-2-yl)-pyrrolidin-1-yl]-methanone |
| 205 | (3-chloro-2-fluoro-phenyl)-[2-(5-thiophen-2-yl-[1,3,4]oxadiazol-2-yl)-pyrrolidin-1-yl]-methanone |
| 206 | (2-chloro-phenyl)-[2-(5-phenyl-[1,3,4]oxadiazol-2-yl)-pyrrolidin-1-yl]-methanone |
| 207 | [2-(5-biphenyl-4-yl-[1,3,4]oxadiazol-2-yl)-pyrrolidin-1-yl]-m-tolyl-methanone |
| 208 | 1-{2-[5-(4-chloro-phenyl)-[1,3,4]oxadiazol-2-yl]-pyrrolidin-1-yl}-butan-1-one |
| 209 | {2-[5-(4-chloro-phenyl)-[1,3,4]oxadiazol-2-yl]-pyrrolidin-1-yl}-pyridine-2-yl-methanone |
| 210 | [2-(5-phenyl-[1,3,4]oxadiazol-2-yl)-pyrrolidin-1-yl]-(4-trifluoromethyl-phenyl)-methanone |
| 211 | 2-biphenyl-4-yl-5-[1-(4-chloro-benzylsulfonyl)-pyrrolidin-2-yl]-[1,3,4]oxadiazole |
| 212 | 1-[2-(5-biphenyl-4-yl-[1,3,4]oxadiazol-2-yl)-pyrrolidin-1-yl]-2-phenoxy-ethanone |
| 213 | 2-phenyl-5-[1-(toluene-4-sulfonyl)-pyrrolidin-2-yl]-[1,3,4]oxadiazole |
| 214 | [2-(5-phenyl-[1,3,4]oxadiazol-2-yl)-pyrrolidin-1-yl]-(3-trifluoromethoxy-phenyl)-methanone |
| 215 | [2-(5-biphenyl-4-yl-[1,3,4]oxadiazol-2-yl)-pyrrolidin-1-yl]-(4-propyl-phenyl)-methanone |
| 216 | benzoic acid 2-[2-(5-phenyl-[1,3,4]oxadiazol-2-yl)-pyrrolidin-1-carbonyl]-benzylester |
| 217 | {2-[5-(4-chloro-phenyl)-[1,3,4]oxadiazol-2-yl]-pyrrolidin-1-yl}-(4-nitro-phenyl)-methanone |
| 218 | 2-phenoxy-1-[2-(5-thiophen-2-yl-[1,3,4]oxadiazol-2-yl)-pyrrolidin-1-yl]-propan-1-one |
| 219 | 2-(4-chloro-phenyl)-1-[2-(5-phenyl-[1,3,4]oxadiazol-2-yl)-pyrrolidin-1-yl]-ethanone |
| 220 | [2-(5-biphenyl-4-yl-[1,3,4]oxadiazol-2-yl)-pyrrolidin-1-yl]-(2-chloro-5-trifluoromethyl-phenyl)-methanone |
| 221 | (2,3-difluoro-phenyl)-[2-(5-phenyl-[1,3,4]oxadiazol-2-yl)-pyrrolidin-1-yl]-methanone |
| 222 | 2-biphenyl-4-yl-5-[1-(3-chloro-4-fluoro-benzylsulfonyl)-pyrrolidin-2-yl]-[1,3,4]oxadiazole |
| 223 | (3,4-difluoro-phenyl)-[2-(5-thiophen-2-yl-[1,3,4]oxadiazol-2-yl)-pyrrolidin-1-yl]-methanone |
| 224 | 1-[2-(5-biphenyl-4-yl-[1,3,4]oxadiazol-2-yl)-pyrrolidin-1-yl]-2-propyl-pentan-1-one |
| 225 | (3-fluoro-4-trifluoromethyl-phenyl)-[2-(5-pyridin-4-yl-[1,3,4]oxadiazol-2-yl)-pyrrolidin-1-yl]-methanone |

-continued

| Example ple no. | Compound according to the invention |
|---|---|
| 226 | (6-chloro-2-fluoro-3-methyl-phenyl)-{2-[5-(4-chloro-phenyl)-[1,3,4]oxadiazol-2-yl]-pyrrolidin-1-yl}-methanone |
| 227 | (2-phenyl-cyclopropyl)-[2-(5-phenyl-[1,3,4]oxadiazol-2-yl)-pyrrolidin-1-yl]-methanone |
| 228 | (4-bromo-3-methyl-phenyl)-[2-(5-phenyl-[1,3,4]oxadiazol-2-yl)-pyrrolidin-1-yl]-methanone |
| 229 | [2-(5-biphenyl-4-yl-[1,3,4]oxadiazol-2-yl)-pyrrolidin-1-yl]-(2,3-dimethyl-phenyl)-methanone |
| 230 | [2-(5-biphenyl-4-yl-[1,3,4]oxadiazol-2-yl)-pyrrolidin-1-yl]-(3-chloro-phenyl)-methanone |
| 231 | [2-(5-biphenyl-4-yl-[1,3,4]oxadiazol-2-yl)-pyrrolidin-1-yl]-(2,3-difluoro-4-methyl-phenyl)-methanone |
| 232 | (2-chloro-6-fluoro-phenyl)-{2-[5-(4-chloro-phenyl)-[1,3,4]oxadiazol-2-yl]-pyrrolidin-1-yl}-methanone |
| 233 | [2-(5-biphenyl-4-yl-[1,3,4]oxadiazol-2-yl)-pyrrolidin-1-yl]-(5-tert-butyl-2-methyl-2H-pyrazol-3-yl)-methanone |
| 234 | {2-[5-(4-chloro-phenyl)-[1,3,4]oxadiazol-2-yl]-pyrrolidin-1-yl}-(2,3-dichloro-phenyl)-methanone |
| 235 | 2-(5-pyridin-3-yl-[1,3,4]oxadiazol-2-yl)-pyrrolidin-1-carboxylic acid (4-ethoxy-phenyl)-amide |
| 236 | 2-(5-pyridin-3-yl-[1,3,4]oxadiazol-2-yl)-pyrrolidin-1-carboxylic acid (2,5-dichloro-phenyl)-amide |
| 237 | 2-[5-(3-methoxy-phenyl)-[1,3,4]oxadiazol-2-yl]-pyrrolidin-1-carboxylic acid 4-fluoro-benzylamide |
| 238 | 2-[5-(2-fluoro-phenyl)-[1,3,4]oxadiazol-2-yl]-pyrrolidin-1-carboxylic acid (2,5-dimethoxy-phenyl)-amide |
| 239 | 2-(5-biphenyl-4-yl-[1,3,4]oxadiazol-2-yl)-pyrrolidin-1-carboxylic acid(2,5-dimethoxy-phenyl)-amide |
| 240 | 2-(5-biphenyl-4-yl-[1,3,4]oxadiazol-2-yl)-pyrrolidin-1-carboxylic acid(2,5-difluoro-phenyl)-amide |
| 241 | 2-(5-biphenyl-4-yl-[1,3,4]oxadiazol-2-yl)-pyrrolidin-1-carboxylic acid (3-cyano-phenyl)-amide |
| 242 | 2-(5-biphenyl-4-yl-[1,3,4]oxadiazol-2-yl)-pyrrolidin-1-carboxylic acid (3-cyano-phenyl)-amide |
| 243 | 2-[5-(3-methoxy-phenyl)-[1,3,4]oxadiazol-2-yl]-pyrrolidin-1-carboxylic acid (3-cyano-phenyl)-amide |
| 244 | 2-(5-phenyl-3-yl[1,3,4]oxadiazol-2-yl)-pyrrolidin-1-carboxylic acid (4-chloro-3-trifluoromethyl-phenyl)-amide |
| 245 | 2-(5-phenyl-[1,3,4]oxadiazol-2-yl)-pyrrolidin-1-carboxylic acid (4-methoxy-phenyl)-amide |
| 246 | 2-(5-biphenyl-4-yl-[1,3,4]oxadiazol-2-yl)-pyrrolidin-1-carboxylic acid (4-trifluoromethoxy-phenyl)-amide |
| 247 | 1-{2-[5-(3-chloro-phenyl)-[1,3,4]oxadiazol-2-yl]-pyrrolidin-1-yl}-3-cyclopentyl-propan-1-one |
| 248 | 1-{2-[5-(3-chloro-phenyl)-[1,3,4]oxadiazol-2-yl]-pyrrolidin-1-yl}-pentan-1-one |

The compounds according to the invention were produced by the above-described process, which will be illustrated in detail with reference to the following two examples:

Example 247

1-{2-[5-3-chloro-phenyl)-[1,3,4]oxadiazol-2-yl]-pyrrolidin-1-yl}-3cyclopentyl-propan-1-one 1st stage

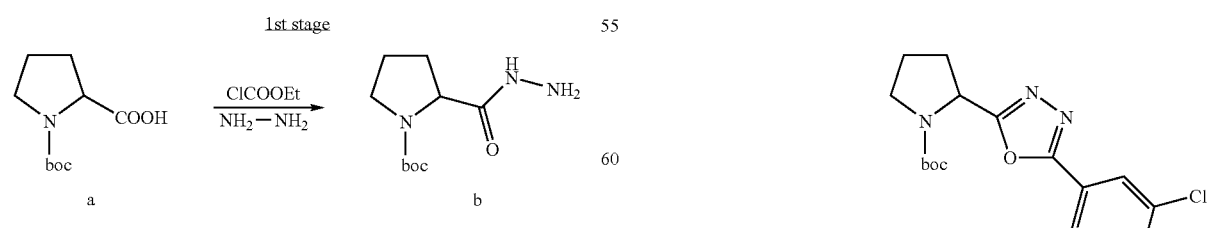

A solution of ethyl chloroformate (10.33 ml) in 20 ml dry THF was added dropwise within 5 min to a stirred solution of Boc-(L)-proline (23.27 g), cooled to −15° C., and 15.07 ml triethylamine in 250 ml dry THF. The mixture was stirred for a further 30 min at −15° C. The cold reaction mixture was filtered off, the filtrate evaporated to a volume of about 125 ml and then added dropwise within 15 min to a stirred and cooled (0° C.) solution of hydrazine monohydrate (10.5 ml) in 150 ml dry THF. The reaction mixture was stirred for a further 15 min at 0° C. and then for a further 2 hours at room temperature. The solution was decanted off from a milky white oil at the bottom of the flask and evaporated to dryness. The crude product was used without further purification. Yield: 25.63 g.

2nd stage:

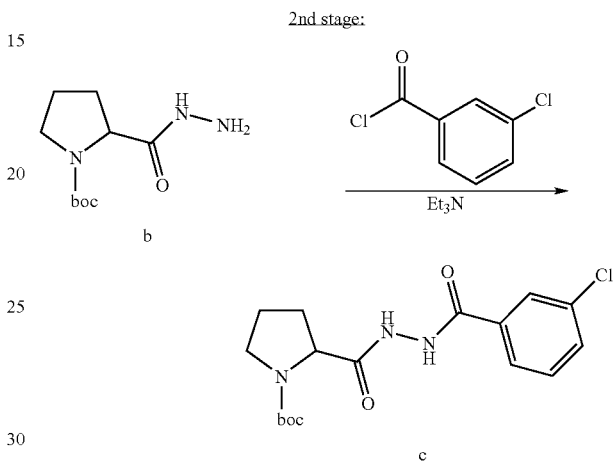

11.42 ml 3-chlorobenzoylchloride in 10 ml dry THF was added dropwise within 5 min to a stirred solution of the hydrazide b (18.6 g), cooled to −15° C., and triethylamine (13 ml) in 180 ml dry THF. The mixture was stirred for a further 20 min at −15° C., 60 min at 0° C. and then 2 hours at room temperature. The reaction mixture was filtered off and the filtrate was evaporated to dryness. The brown, oily crude product was purified by silica gel chromatography (DCM, 3.75% methanol). Yield 18.67 g.

3rd stage

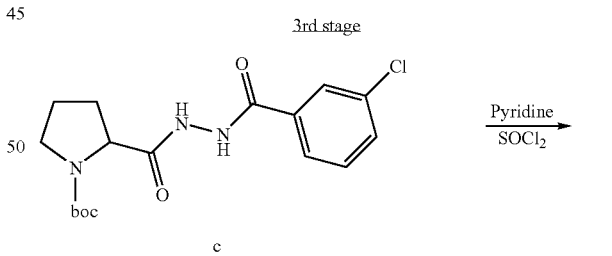

The ring was closed in anhydrous diethyl ether under a nitrogen atmosphere. 6.3 g SOCl₂ were added dropwise to a solution of the hydrazide c (15 g) cooled to 0° C. and 8.4 g pyridine in dry diethyl ether. The reaction mixture was stirred for 2 hours at 0° C. The resulting salt was filtered out, and the filtrate evaporated at 0° C. The residue was dissolved in 500 ml toluene and heated under reflux under a nitrogen atmosphere. After 2 hours the solution was evaporated to dryness and purified by silica gel chromatography (diethyl ether). Yield: 13 g.

4th stage

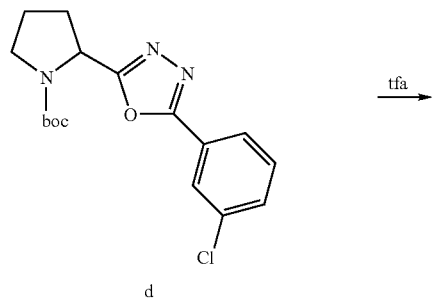

d

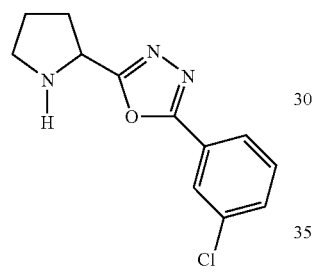

e 13 g of the oxadiazole derivative d were dissolved in 25 ml DCM. After adding 5 ml trifluoroacetic acid (Tfa) the mixture was stirred for 6 days under a nitrogen atmosphere. After a further addition of 10 ml trifluoroacetic acid the reaction mixture was stirred for a further 6 hours and then evaporated to dryness. 100 ml of a saturated, aqueous NaHCO₃ solution and 100 ml DCM were added and the aqueous phase extracted with DCM a further two times. The combined organic phases were dried over Na₂SO₄ and evaporated to dryness. The product was used without further purification. Yield: 10 g.

5th stage

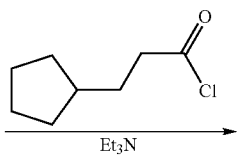

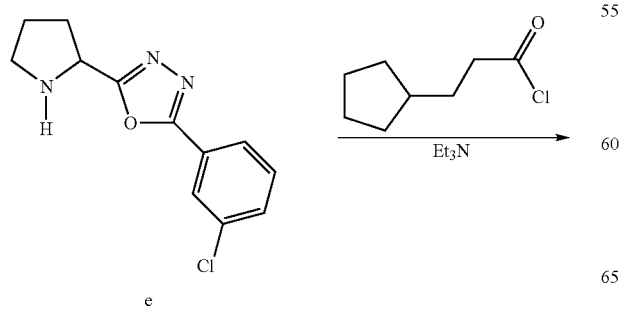

e

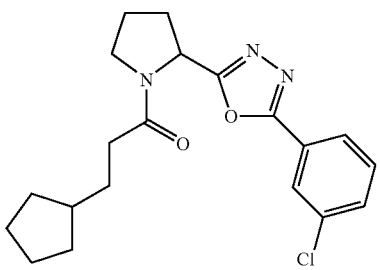

f 804 mg of the oxadiazole derivative e were dissolved in 9 ml DCM. 326 mg triethylamine and 517 mg 3-cyclopentylpropionylchloride in 1 ml DCM were added at a temperature of −20° C. The reaction mixture was stirred for 2 hours at −20° C. and then evaporated to dryness. The product was purified by column chromatography (silica gel, ethyl acetate/heptane 1:2, then basic Allox, ethyl acetate/heptane 1:2). Yield 170 mg.

Example 248

1-{2-[5-3-chloro-phenyl)-[1,3,4]oxadiazol-2-yl]-pyrrolidin-1-yl}-pentan-1-one

Stages 1–4 corresponded to stages 1–4 of Example 247.

5th stage:

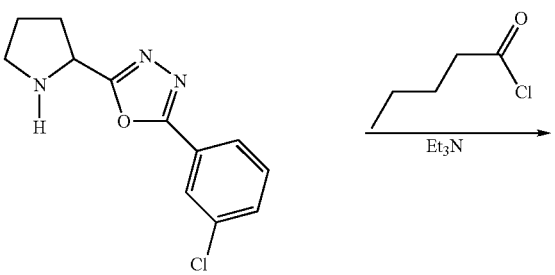

e

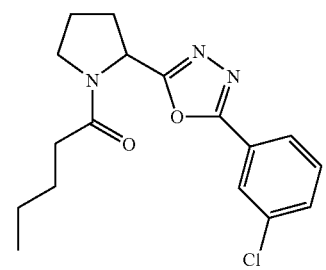

g 1.3 g of the oxadiazole derivative e was dissolved in 9 ml DCM. 1 g triethylamine and 620 mg 3-valeroylchloride in 1 ml DCM were added at a temperature of −20° C. The reaction mixture was stirred for 2 hours at −20° C. and then evaporated to dryness. The product was purified by column chromatography (silica gel, ethyl acetate/heptane 1:2, then basic Allox, ethyl acetate/heptane 1:2). Yield: 181 mg.

Pharmacological Tests

Tests of Inhibition of Serotonin Re-Uptake (5HT-Uptake Inhibition)

To be able to carry out these studies in vitro, synaptosomes were freshly isolated from rat brain areas. What is known as a "$P_2$" fraction was used in each case. This was prepared in accordance with Gray and Whittaker's directions (E. G. Gray and V. P. Whittaker (1962) J. Anat. 76, 79–88). These vesicular particles were isolated from the medulla+pons region of male rats' brains for 5HT uptake. A detailed description of the method may be found in the literature (M. Ch. Frink, H.-H. Hennies, W. Englberger, M. Haurand and B. Wilffert (1996) Arzneim. -Forsch./Drug Res. 46 (III), 11,1029–1036). The 5HT-uptake inhibition of the following compounds was tested by way of example:

TABLE 1

| Compound according to Example No. | 5HT uptake, % inhibition |
| --- | --- |
| 4 | 72 |
| 5 | 81 |
| 6 | 84 |
| 7 | 64 |
| 12 | 54 |
| 13 | 67 |
| 14 | 69 |
| 21 | 53 |
| 22 | 60 |
| 30 | 60 |
| 61 | 50 |
| 67 | 50 |
| 84 | 61 |
| 85 | 61 |
| 86 | 73 |
| 92 | 58 |
| 94 | 50 |
| 101 | 54 |
| 109 | 54 |
| 134 | 55 |
| 164 | 80 |
| 165 | 76 |
| 166 | 78 |
| 173 | 62 |
| 174 | 61 |
| 181 | 62 |
| 182 | 52 |

Investigation of Analgesic Efficacy by Testing Writhing in Mice

The investigation into analgesic efficacy was performed by phenylquinone-induced writhing in mice (modified after: I. C. Hendershot and J. Forsaith (1959), J. Pharmacol. Exp. Ther. 125, 237–240). Male NMRI mice weighing from 25 to 30 g were used for this purpose. 10 minutes after intravenous administration of the compounds tested, groups of 10 animals per substance dose received 0.3 ml/mouse of a 0.02% aqueous solution of phenylquinone (phenylbenzoquinone, Sigma, Deisenhofen; solution prepared by adding 5% of ethanol and stored in a water bath at 45° C.) administered intraperitoneally. The animals were placed individually into observation cages. A pushbutton counter was used to record the number of pain-induced stretching movements (writhing reactions=straightening of the torso with stretching of the rear extremities) for 5–20 minutes after phenylquinone administration. The control was provided by animals which received only physiological common salt solution. All substances were tested at the standard dosage of 10 mg/kg. The percentage inhibition (% inhibition) of the writhing reactions by a substance was calculated according to the following formula:

$$\% \text{ inhibition} = 100 - \frac{\text{writhing reactions of treated animals}}{\text{writhing reactions of control animals}} * 100$$

For some substances the $ED_{50}$-value of the writhing reaction with a 95% confidence range was calculated by regression analysis from the dose-dependent reduction in the writhing reactions compared with simultaneously investigated phenylquinone control groups (evaluation program Martens EDV Service, Eckental). The investigated compounds according to the invention exhibited good analgesic activity. The results are summarised in the following Table 2.

TABLE 2

| Example No. | % inhibition of writhing reaction by intravenous administration of 10 mg/kg |
| --- | --- |
| 247 | 33 |
| 248 | 45 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A substituted 2-pyrrolidin-2-yl-[1,3,4]-oxadiazole compound corresponding to formula I

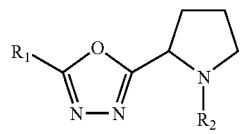

wherein
$R_1$ represents aryl or heteroaryl,
$R_2$ represents H, $SO_2R^3$ or $COR^4$;
$R^3$ and $R^4$ independently of one another represent $C_{1-10}$ alkyl, $C_{3-10}$ cycloalkyl, ($C_{1-6}$ alkyl)-$C_{3-10}$ cycloalkyl, aryl, ($C_{1-6}$ alkyl)-aryl, heterocyclyl, radicals of carboxylic acid esters with 3–10 carbon atoms, dimethyl amide or $NR^5R^6$, and
$R^5$ and $R^6$ independently of one another represent H or aryl.

2. A compound according to claim 1, wherein
$R_1$ represents aryl or heteroaryl, wherein
aryl represents unsubstituted phenyl or phenyl substituted by F, Cl, O-alkyl or phenyl, and
heteroaryl represents pyridinyl or thienyl,
$R_2$ represents H, $SO_2R^3$ or $COR^4$, wherein
$R^3$ and $R^4$ independently of one another represent $C_{1-10}$ alkyl, $C_{3-10}$ cycloalkyl, ($C_{1-6}$ alkyl)-$C_{3-10}$ cycloalkyl, aryl, $C_{1-6}$ alkyl)-aryl, heterocyclyl, radicals of carboxylic acid esters with 3–10 carbon atoms, dimethylamide or $NR^5R^6$, wherein C$_{1-10}$ alkyl represents methyl, propyl, butyl, butenyl, isobutyl, pentyl, pent-3-yl, hept-3-yl, hept-4-yl, 2,2-dimethylpropyl, CH$_2$OCH$_3$, CH$_2$O(CH$_2$)$_2$OCH$_3$, or CH(benzyl)NSO$_2$C$_6$H$_4$CH$_3$;

C$_{3-10}$ cycloalkyl represents cyclopropyl, cyclobutyl, cyclopentyl, adamantan-1-yl, 2-phenyl-cyclopropyl or 4,7,7-trimethyl-2-oxa-bicyclo[2.2.1]heptan-3-on-1-yl;

(C$_{1-6}$ alkyl)-C$_{3-10}$ cycloalkyl represents CH$_2$-cyclopentyl, (CH$_2$)$_2$-cyclopentyl or 7,7-dimethyl-1-methyl-bicyclo[2.2.1]heptan-2-one;

aryl represents phenyl, benzyl or naphthyl unsubstituted, singly substituted or multiply identically or differently substituted by phenyl, NO$_2$, C$_{1-6}$ alkyl, in which the carbon atom chain is optionally interrupted by one or more of the heteroatoms N, O or S, O-alkyl, CO$_2$-alkyl, C(=O)C$_{1-6}$ alkyl, CH$_2$OC(=O)C$_6$H$_5$, F, Cl, Br, N(CH$_3$)$_2$, OCF$_3$, CF$_3$, SCHF$_2$, SCF$_3$ or (C=O)CH$_3$;

(C$_{1-6}$ alkyl)-aryl represents 3,4-dimethoxyphenyl-CH$_2$, 4-chlorophenyl-CH$_2$, phenyl-CH=CH, benzyl-OCH$_2$, phenyl-(CH$_2$)$_2$, 2-bromophenyl-CH$_2$, 1-phenyl-propyl, 2-chlorophenyl-CH=CH, 3-trifluoromethyl-phenyl-CH=CH, phenoxy-CH$_2$, phenoxy-(CH$_2$)$_3$ or phenoxy-CH(CH$_3$);

heterocyclyl represents pyridinyl, isoxazole, thienyl, furanyl, triazole, benzooxadiazole, thiadiazole, pyrazole or isoquinoline, unsubstituted, singly substituted or multiply identically or differently substituted by Cl, C$_{1-6}$ alkyl, phenyl, which is in turn unsubstituted or singly substituted or multiply identically or differently substituted by Cl or C$_{1-6}$ alkyl, CF$_3$, C(=O)CF$_3$ or SCH$_3$;

the radicals of carboxylic acid esters with 3–10 carbon atoms represent
CH$_3$OC(=O)CH$_2$
CH$_3$OC(=O)(CH$_2$)$_3$
CH$_3$CH$_2$OC(=O)CH$_2$
CH$_3$CH$_2$OC(=O)(CH$_2$)$_2$
CH$_3$C(=O)OCH$_2$
CH$_3$C(=O)OC(CH$_3$)$_2$ or
CH$_3$C(=O)OCH(C$_6$H$_5$), and R$^5$ and R$^6$ independently of one another represent H or aryl, wherein
aryl represents benzyl or phenyl, respectively singly substituted or multiply identically or differently substituted by F, Cl, O-alkyl, CN, CF$_3$ or OCF$_3$.

3. A compound according to claim 1, wherein
R$_1$ represents phenyl, bisphenyl-4-yl, 3-methoxyphenyl, 4-chlorophenyl, 2-fluorophenyl, pyridin-3-yl, pyridin-4-yl or thiophen-2-yl;

R$_2$ represents H, SO$_2$R$^3$ or COR$^4$, wherein
R$^3$ and R$^4$ independently of one another represent CH$_3$CH$_2$OCO(CH$_2$)$_2$—, 2,4-dimethoxy-phenyl, 2-chloro-pyridin-3-yl, 2-chloro-pyridin-4-yl, 7,7-dimethyl-1-methyl-bicyclo[2.2.1]heptan-2-one, 3-dimethyl-amino-phenyl, 3,4-dimethoxy-phenyl, 2,5-dimethoxy-phenyl, 4-chloro-phenyl, —CH(benzyl)NSO$_2$C$_6$H$_4$CH$_3$, 4,5-dichloro-thiophen-2-yl, 2,4,6-trimethylphenyl, 4-chloro-phenoxy-methyl, C$_6$H$_5$CH=CH—, 5-methyl-2-phenyl-2H-[1,2,3]triazol-4-yl, 2,4-difluorophenyl, 2,6-difluorophenyl, 4-bromo-phenyl, 4-ethoxy-phenyl, 4-trifluoromethoxyphenyl-phenyl, 2,5-bis-trifluoromethyl-phenyl, 1-phenyl-5-propyl-1H-pyrazol-4-yl, 3-methoxy-phenyl, 2-methyl-6-trifluoromethyl-pyridin-3-yl, 4-trifluoromethylsulfanyl-phenyl, 2,2,2-trifluoro-1-3,4-dihydro-1H-isoquinoline-2-yl-ethanone or NR$^5$R$^6$, wherein R$^5$ and R$^6$ independently of one another represent H or 3-methoxyphenyl, 4-methoxyphenyl, 4-ethoxyphenyl, 2,5-dimethoxy-phenyl, 2,5-dichlorophenyl, 2,5-difluorophenyl, 4-fluorobenzyl, 4-chloro-3-trifluoromethyl-phenyl, 4-trifluoromethoxyphenyl or 3-cyanophenyl.

4. A substituted 2-pyrrolidin-2-yl-[1,3,4]-oxadiazole compound according to claim 1, selected from the group consisting of:
4-oxo-4-[2-(5-pyridin-4-yl-[1,3,4]oxadiazol-2-yl)-pyrrolidin-1-yl]-butyric acid ethyl ester,
(2,4-dimethoxy-phenyl)-[2-(5-pyridin-4-yl-[1,3,4]oxadiazol-2-yl)-pyrrolidin-1-yl]-methanone,
(2-chloro-pyridin-3-yl)-[2-(5-pyridin-4-yl-[1,3,4]oxadiazol-2-yl)-pyrrolidin-1yl]-methanone,
7,7-dimethyl-1-[2-(5-pyridin-4-yl-[1,3,4]oxadiazol-2-yl)-pyrrolidin-1-sulfonylmethyl]-bicyclo[2.2.1]heptan-2-one,
(3-dimethyl-phenyl)-[2-(5-pyridin-3-yl-[1,3,4]oxadiazol-2-yl)-pyrrolidin-1-yl]-methanone,
2-(3,4-dimethoxy-phenyl)-1-[2-(5-pyridin-4-yl-[1,3,4]oxadiazol-2-yl)-pyrrolidin-1-yl]-ethanone,
[2-(5-biphenyl-4-yl-[1,3,4]oxadiazol-2-yl)-pyrrolidin-1-yl]-(4-chloro-phenyl)-methanone,
N-{1-benzyl-2-oxo-2-[2-(5-pyridin-4-yl-[1,3,4]oxadiazol-2-yl)-pyrrolidin-1-yl]-ethyl}-4-methyl-benzylsulfonamide,
4-{5-[1-(4,5-dichloro-thiophene-2-sulfonyl)-pyrrolidin-2-yl]-[1,3,4]oxadiazol-2-yl}-pyridine,
3-{5-[1-(2,5-dimethoxy-benzylsulfonyl)-pyrrolidin-2-yl]-[1,3,4]oxadiazol-2-yl}-pyridine,
2-(2-fluoro-phenyl)-5-[1-(2,4,6-trimethyl-benzylsulfonyl)-pyrrolidin-2-yl]-[1,3,4]oxadiazole,
2-(4-chloro-phenoxy)-1-[2-(5-pyridin-4-yl-[1,3,4]oxadiazol-2-yl)-pyrrolidin-1-yl]-ethanone,
3-phenyl-1-[2-(5-phenyl-[1,3,4]oxadiazol-2-yl)-pyrrolidin-1-yl]-propenone,
(5-methyl-2-phenyl-[1,2,3]triazol-4-yl)-[2-(5-pyridin-4-yl-[1,3,4]oxadiazol-2-yl)-pyrrolidin-1-yl]-methanone,
3-{5-[1-(2,4-difluoro-benzylsulfonyl)-pyrrolidin-2-yl]-[1,3,4]oxadiazol-2-yl}-pyridine,
(4-bromo-phenyl)-{2-[5-(3-methoxy-phenyl)-[1,3,4]oxadiazol-2-yl]-pyrrolidin-1-yl}-methanone,
(2-chloro-pyridin-4-yl)-{2-[5-(3-methoxy-phenyl)-[1,3,4]oxadiazol-2-yl]-pyrrolidin-1-yl}-methanone,
(2,6-difluoro-phenyl)-[2-(5-pyridin-4-yl-[1,3,4]oxadiazol-2-yl)-pyrrolidin-1-yl]-methanone,
(4-ethoxy-phenyl)-[2-(5-phenyl-[1,3,4]oxadiazol-2-yl)-pyrrolidin-1-yl]-methanone,
3-{5-[1-(4-trifluoromethoxy-benzylsulfonyl)-pyrrolidin-2-yl]-[1,3,4]oxadiazol-2-yl}-pyridine,
(2,5-bis-trifluoromethyl-phenyl)-{2-[5-(4-chloro-phenyl)-[1,3,4]oxadiazol-2-yl]-pyrrolidin-1-yl}-methanone,
(2,5-bis-trifluoromethyl-phenyl)-[2-(5-thiophen-2-yl-[1,3,4]oxadiazol-2-yl)-pyrrolidin-1-yl]-methanone,
(1-phenyl-5-propyl-1H-pyrazol-4-yl)-[2-(5-pyridinyl-yl-[1,3,4]oxadiazol-2-yl)-pyrrolidin-1-yl]-methanone,
(2,3-difluoro-phenyl)-{2-[5-(3-methoxy-phenyl)-[1,3,4]oxadiazol-2-yl]-pyrrolidin-1-yl}-methanone,
(2-methyl-6-trifluoromethyl-pyridin-3-yl)-[2-(5-phenyl-[1,3,4]oxadiazol-2-yl)-pyrrolidin-1-yl]-methanone,
[2-(5-phenyl-[1,3,4]oxadiazol-2-yl)-pyrrolidin-1-yl]-(4-trifluormethylsulfanyl-phenyl)-methanone,
2,2,2-trifluoro-1-{7-[2-(5-pyridin-4-yl-[1,3,4]oxadiazol-2-yl)-pyrrolidin-1-sulfonyl]-3,4-dihydro-1H-isoquinolin-2-yl}-ethanone,
1-{2-[5-(3-chloro-phenyl)-[1,3,4]oxadiazol-2-yl]-pyrrolidin-1-yl}-3-cyclopentyl-propan-1-one, and
1-{2-[5-(3-chloro-phenyl)-[1,3,4]oxadiazol-2-yl]-pyrrolidin-1-yl}-pentan-1-one.

5. A process for producing a substituted 2-pyrrolidin-2-yl-[1,3,4]-oxadiazole compound corresponding to formula I according to claim 1, comprising the following synthesis pattern:

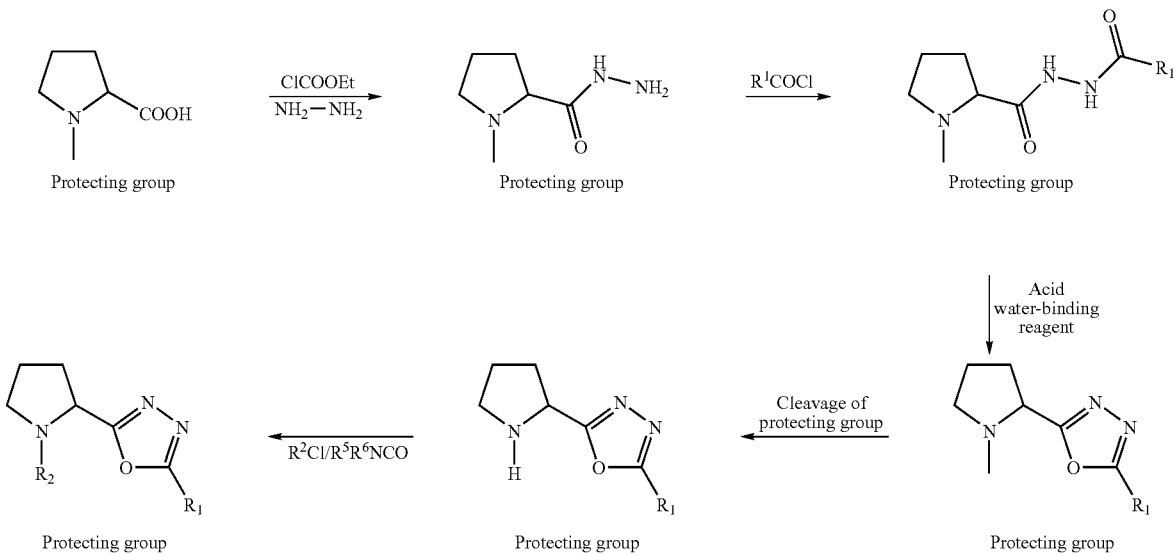

6. A pharmaceutical composition comprising a compound according to claim 1 and at least one pharmaceutical carrier or auxiliary.

7. A method of treating or inhibiting at least one condition selected from the group consisting of pain, and, said method comprising administering to a patient in need thereof a pharmaceutically effective amount of a compound according to claim 1.

8. A method according to claim 7, wherein said condition is pain.

9. A method according to claim 7, wherein said condition is depression.

* * * * *